(12) United States Patent
Gage et al.

(10) Patent No.: US 11,045,339 B2
(45) Date of Patent: Jun. 29, 2021

(54) APPARATUS AND METHOD FOR IMPLANTING AN ARTERIOVENOUS GRAFT

(71) Applicant: Innavasc Medical Inc., Durham, NC (US)

(72) Inventors: Shawn M. Gage, Raleigh, NC (US); Joseph Knight, Durham, NC (US); Michael Lawson, Durham, NC (US); Craig Nichols, Durham, NC (US)

(73) Assignee: InnAVasc Medical, Inc., Raleigh, NC (US)

( * ) Notice: Subject to any disclaimer, the term of this patent is extended or adjusted under 35 U.S.C. 154(b) by 0 days.

(21) Appl. No.: 16/723,211

(22) Filed: Dec. 20, 2019

(65) Prior Publication Data

US 2020/0197205 A1 Jun. 25, 2020

Related U.S. Application Data

(60) Provisional application No. 62/940,438, filed on Nov. 26, 2019, provisional application No. 62/783,187, filed on Dec. 20, 2018.

(51) Int. Cl.
*A61F 2/966* (2013.01)
*A61F 2/95* (2013.01)

(52) U.S. Cl.
CPC ............ *A61F 2/966* (2013.01); *A61F 2/9522* (2020.05); *A61F 2002/9665* (2013.01)

(58) Field of Classification Search
CPC .. A61F 2/95; A61F 2/962; A61F 2/966; A61F 2002/9505; A61F 2002/9522; A61F 2002/9665
See application file for complete search history.

(56) References Cited

U.S. PATENT DOCUMENTS

| 5,306,240 A | 4/1994 | Berry |
| 6,254,628 B1 * | 7/2001 | Wallace ........... A61B 17/12118 606/108 |
| 7,628,795 B2 | 12/2009 | Karwoski |
| 7,727,268 B2 | 6/2010 | Cunniffe et al. |

(Continued)

FOREIGN PATENT DOCUMENTS

WO 2020132505 6/2020

OTHER PUBLICATIONS

Gage, Shawn; International Search Report and Written Opinion for PCT Application No. PCT/US2019/067954, filed Dec. 20, 2019; 23 pages.

*Primary Examiner* — Ashley L Fishback
(74) *Attorney, Agent, or Firm* — Taylor English Duma LLP

(57) ABSTRACT

An apparatus is provided for subcutaneous implantation in a patient using a tunneling instrument. The implantation apparatus comprises a vascular graft and a connector adapted to couple a distal end of the tunneling instrument and a proximal end of the graft. The connector comprises a tip, a first end of the tip configured to be received within the proximal end of the graft, a clip for securing the graft to the tip, and a coupler for a rotatable connection of the tip to the tunneling instrument such that the tip is rotatable about its longitudinal axis relative to the coupler to facilitate attachment of the graft to the tunneling instrument. The implantation apparatus may further comprise a removable sheath configured to substantially cover the length of the graft.

4 Claims, 22 Drawing Sheets

(56) References Cited

U.S. PATENT DOCUMENTS

| | | |
|---|---|---|
| 8,177,832 B2 | 5/2012 | Armstrong et al. |
| 8,292,938 B2 | 10/2012 | Case et al. |
| 8,545,544 B2 | 10/2013 | Spenser et al. |
| 8,622,886 B2 | 1/2014 | Young et al. |
| 9,125,657 B2 | 9/2015 | Ray et al. |
| 9,345,566 B2 | 5/2016 | Bosel |
| 9,387,101 B2 | 7/2016 | Dorn et al. |
| 9,622,893 B2 | 4/2017 | Huser |
| 9,687,369 B2 | 6/2017 | Dorn et al. |
| 9,808,366 B2 | 11/2017 | Dorn |
| 10,045,868 B2 | 8/2018 | Cully et al. |
| 10,149,750 B2 | 12/2018 | Wagner et al. |
| 10,271,979 B2 | 4/2019 | Dorn et al. |
| 10,328,243 B2 | 6/2019 | Spear et al. |
| 2006/0015171 A1* | 1/2006 | Armstrong ....... A61B 17/12022 623/1.12 |
| 2006/0135949 A1 | 6/2006 | Rome et al. |
| 2006/0173467 A1 | 8/2006 | Karwoski et al. |
| 2009/0192586 A1* | 7/2009 | Tabor .................... A61F 2/2412 623/1.11 |
| 2013/0304185 A1 | 11/2013 | Newell |
| 2017/0072129 A1 | 3/2017 | Slager et al. |
| 2018/0078353 A1 | 3/2018 | Alexander et al. |
| 2018/0193178 A1 | 7/2018 | Zukowski et al. |
| 2018/0264188 A1 | 9/2018 | Ash |

* cited by examiner

APPARATUS AND METHOD FOR IMPLANTING AN ARTERIOVENOUS GRAFT

CROSS-REFERENCES TO RELATED APPLICATIONS

This application claims the benefit of U.S. Provisional Application No. 62/783,187, filed Dec. 20, 2018, and U.S. Provisional Application No. 62/940,438, filed Nov. 26, 2019, the contents of both of which are incorporated herein in their entirety.

BACKGROUND

An apparatus and method are described for implanting an arteriovenous graft and, more particularly, an apparatus and method for use in forming a subcutaneous anatomical tunnel for implanting the arteriovenous graft, including use of a removable sheath enclosing the graft during implantation.

An arteriovenous graft is a tubular device that is suitable for implantation in the body to redirect flow of blood between blood vessels. Surgical implantation of the arteriovenous graft requires placement of the graft within subcutaneous tissue. An initial step in the implantation procedure is the creation of a subcutaneous anatomic pathway for the arteriovenous graft, which is commonly called a graft tunnel, between anastomotic sites for passage of the vascular graft. This is a required surgical step in peripheral vascular procedures for all peripheral, vascular access and extraanatomical graft locations. The arteriovenous graft is positioned in the tunnel within the bodily tissue for fixation of the graft to an existing peripheral vessel to form a bypass around the vessel, or a portion thereof, or connection of an artery and vein to form an arteriovenous shunt. The vascular graft may also connect an artery to an artery.

A conventional tunneling device includes an elongated rigid rod having a handle on a proximal end and a bullet-shaped tip at a distal end. The rod may vary in size and shape and may have a straight shaft, a curved shaft or a semicircular shaft, which allows for a variety of graft placement positions and locations. In the tunneling procedure, a proximal incision and a distal incision are made at a chosen area of anastomosis. The tip at the distal end of the tunneling device is inserted into the proximal incision. The tip of the tunneling device is then forcefully passed through the subcutaneous tissue creating a path between the incisions by blunt dissection until the tip protrudes from the distal incision. Once the tip is exposed, a proximal end of the arteriovenous graft is tied onto the distal end or the tip of the tunneling device with sterile suture thread. The tunneling instrument and attached arteriovenous graft are then pulled along the path through the recently dissected graft tunnel until the proximal end of the arteriovenous graft extends from the proximal incision. When the arteriovenous graft is appropriately positioned, the graft is cut free from the distal end of the tunneling instrument. An anastomosis is formed around the area of vasculature to be bypassed and the incisions are closed.

The step of pulling the tunneling instrument and attached arteriovenous graft through the graft tunnel requires significant force. The force required depends on a number of factors, including the relative sizes of the graft tunnel and the graft and the material of the graft. Conventional delivery systems for venous and other implantable devices are sometimes covered by a retaining sheath that reduces the friction of passage through the subcutaneous tissue. Following implantation, the sheath is removed by rolling back over the device in order to retract the sheath. A pull member may be provided and connected to the sheath to retract the sheath. In one application, the sheath is folded back onto itself so as to provide an inner sheath and an outer sheath disposed over and extending axially along the device. The outer sheath is attached to the pull member. As the pull member is pulled, the outer sheath moves with it causing the sheath to "roll" with respect to the device, thereby progressively uncovering the device. However, while rolling a sheath during retraction reduces the necessary pulling force as compared to withdrawing the sheath by sliding the sheath over the device, there is still significant force necessary to retract a sheath following implantation of an arteriovenous graft.

For the foregoing reasons, there is a need for an apparatus and method for implanting an arteriovenous graft for minimizing trauma to tissue. The arteriovenous graft may be enclosed within a flexible, expandable sheath configured to surround a length of the tunneling device or the graft. The sheath may be coated on an outside surface with a lubricious substance to provide a low coefficient of friction, allowing the sheath and tunneling device to be easily pushed through tissue. The sheath should be retractable in a reliable manner with a low pulling force for minimizing problems associated with excessive axial forces on the sheath during retraction. The tunneling device should be capable of use with any type of vascular graft including, but not limited to, a natural tissue graft. The apparatus may comprise a tunneling device that allows for delivery of fluid adjacent to the tip during the tunneling process.

SUMMARY

An apparatus is provided for subcutaneous implantation in a patient using a tunneling instrument, including a shaft having a proximal end and a distal end. The implantation apparatus comprises a vascular graft having a proximal end and a distal end and a length between the proximal end and the distal end. A connector is adapted to couple the distal end of the tunneling instrument and the proximal end of the graft. The connector comprises a tip, a first end of the tip configured to be received within the proximal end of the graft, a clip for securing the graft to the tip, and a coupler for a rotatable connection of the tip to the tunneling instrument such that the tip is rotatable about its longitudinal axis relative to the coupler to facilitate attachment of the graft to the tunneling instrument.

In one aspect, the coupler comprises a screw thread formed on an external surface for connection of the coupler to the tunneling instrument. In a further aspect, the coupler comprises a ferrule defining an axial passage for rotatably receiving a proximal end of the tip.

In one embodiment, the implantation apparatus further comprises a removable sheath configured to substantially cover the length of the graft.

In another embodiment, the tip comprises a body including an intermediate portion having a reduced diameter forming a circumferential groove around a periphery, and wherein the clip is positioned in the groove, a portion of the graft being positioned between the clip and the tip within the groove, the clip being crimped about the tip to fix the graft to the tip. The clip is sized and shaped to provide a snap-fit connection within the groove.

In an alternative embodiment, the tip is adapted to be removably attached to the distal end of the tunneling instrument, and wherein the connector is configured for connecting the graft to the tunneling instrument upon removal of the tip. In one aspect, the coupler comprises a frustoconical cone having an axial opening for receiving the graft, a length of the cone including a screw thread formed on an external surface for connection of the cone to the tunneling instrument, wherein a portion of the graft is positioned between the threads of the cone and the tunneling instrument to fix the graft to the tip. In another aspect, the coupler comprises a hollow sleeve for rotatable connection to the tunneling instrument, and a plug received within the proximal end of the graft. The sleeve is configured for receiving the plug such that a portion of the graft is positioned between the plug and the sleeve to fix the graft in the sleeve.

The coupler is adapted to be attached to a synthetic vascular graft, a natural tissue vascular graft or an arteriovenous graft.

An implantable device is also provided for subcutaneous delivery in a patient using a tunneling instrument including a shaft having a proximal end and a distal end. The implantable device comprises a vascular graft having a length, a distal end, a proximal end, an outer surface and a longitudinal axis. A sheath having a length is positioned over a substantial portion of the outer surface of the vascular graft. The sheath has longitudinally spaced perforations along the length of the sheath for permitting tearing of the sheath. The sheath is configured to evert upon application of a longitudinal force to the sheath following implantation of the vascular graft to cause the sheath to move in a proximal direction during removal of the sheath from the implanted graft. Upon eversion and exceeding a tearing strength, the sheath tears progressively along the perforations that are generally oriented in a linear arrangement along the length of the sheath.

In one aspect, two rows of perforations are generally oriented circumferentially opposite to one another. In another aspect, two rows of perforations are generally oriented adjacent and parallel to one another.

In one embodiment, the implantable device further comprises a tether connected to the sheath for applying a pulling force in a proximal direction. One end of the tether may be attached to the sheath at a position adjacent to the distal end of the sheath.

In another embodiment, a sheath having perforations is folded back on itself forming a double wall having an inner portion and an outer portion. The sheath is configured to slide over itself upon application of a longitudinal force to the sheath following implantation of the vascular graft to cause the sheath to tear along the perforations while moving in a proximal direction during removal of the sheath from the implanted graft thus reducing the force necessary to extract the sheath.

A tunneling device is provided for delivery of fluid from a fluid source for use in the subcutaneous placement of a vascular graft in a patient. The tunneling device comprises a rigid hollow rod for forming a subcutaneous path and having a distal end, a proximal end and an interior lumen defining a fluid pathway. The interior lumen is adapted to be in fluid communication with the fluid source. A hollow tapered tip is mounted to the distal end of the rod and has an interior lumen in fluid communication with the lumen in the rod. One of the rod or the tip defines at least one opening for delivery of fluid from the fluid source through the at least one opening.

Another tunneling device is provided for use in the subcutaneous placement of a vascular graft for attachment to a blood vessel in a patient. The tunneling device comprises a rigid rod having a proximal end and a distal end for forming a subcutaneous path. A magnetic tapered tip is at the distal end of the rod. A magnetic wand magnetically engages the tip from external to the skin for longitudinal advancement of the rod and tip along the subcutaneous path.

Yet another tunneling device is provided for use in the subcutaneous placement of a vascular graft in a patient. The tunneling device comprises a rigid helical rod having a proximal end and a distal end. A tapered tip is mounted to the distal end of the rod. In use, the rod forms a helical tunnel when rotated during longitudinal advancement along a subcutaneous path.

A method is provided for using a tunneling device having a distal tip for placement of a vascular graft along a subcutaneous path in a patient. The tunneling device method comprises the steps of forming an incision adjacent to a chosen area of anastomosis and placing markers on the skin indicating a predetermined subcutaneous path. The tunneling device is inserted in the incision for performing blunt dissection of subcutaneous tissue along the path indicated by the markers with the tunneling device. A proximal end of the graft is attached to the tunneling device followed by the step of retracting the tunneling device from the incision until the proximal end of the graft exits the incision. The graft is released from the tunneling device and anastomoses are formed of the ends of the graft to a first blood vessel and a second blood vessel and then the incision is closed. In one aspect, the tip of the tunneling device may be removed before attaching the graft.

Still another tunneling device is provided for use in subcutaneous placement of a vascular graft in a patient. The tunneling device comprises a guide wire and a hollow inflatable conduit coaxially surrounding the guide wire over a substantial portion of its length. The conduit in a delivery configuration collapses against the wire due to confining pressure when inserted subcutaneously into a body. Inflation of the conduit radially expands the conduit to a deployed configuration and spaces the conduit from the wire over substantially the full length of the wire and preventing collapse of the subcutaneous tissue inwardly against the wire. The graft may be introduced into the conduit while the conduit is inflated.

BRIEF DESCRIPTION OF THE DRAWINGS

For a more complete understanding of the apparatus and method for use in forming a subcutaneous anatomical tunnel, reference should now be had to the embodiments shown in the accompanying drawings and described below. In the drawings.

DESCRIPTION

Certain terminology is used herein for convenience only and is not to be taken as a limiting. For example, words such as "upper," "lower," "left," "right," "horizontal," "vertical," "upward," "downward," "top" and "bottom" merely describe the configurations shown in the FIGs. Indeed, the components may be oriented in any direction and the terminology, therefore, should be understood as encompassing such variations unless specified otherwise. The words "interior" and "exterior" refer to directions toward and away from, respectively, the geometric center of the core and designated parts thereof. The terminology includes the words specifically mentioned above, derivatives thereof and words of similar import.

Figure 1:
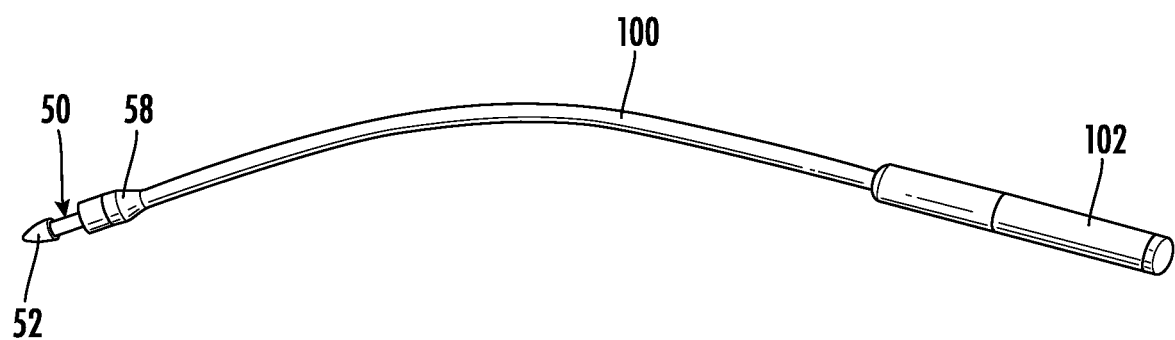
FIG. 1 is a side perspective view of a tunneling instrument including an embodiment of a tip assembly.
Figure 2:
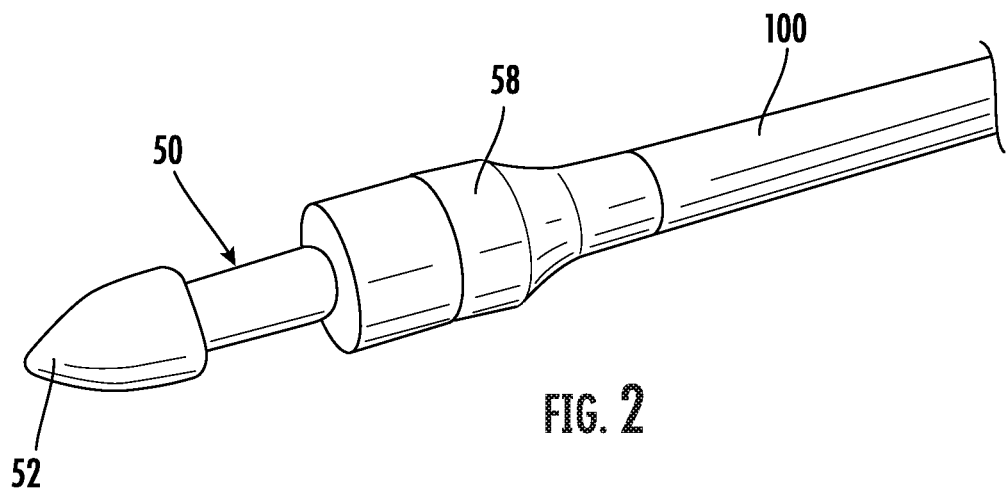
FIG. 2 is a close-up side perspective view of a distal portion of the tunneling instrument and the tip assembly as shown in FIG. 1.
Figure 3:
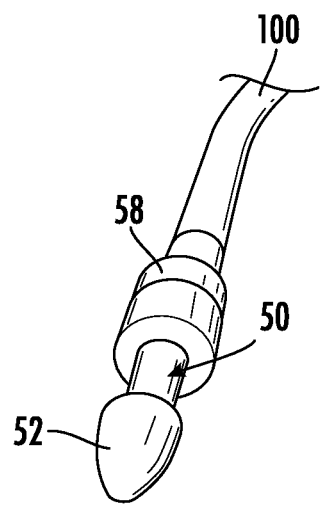
FIG. 3 is a distal end perspective view of the portion of the tunneling instrument and the tip assembly as shown in FIG. 2.

Referring now to the drawings, wherein like reference numerals designate corresponding or similar elements throughout the several views, an embodiment of an apparatus for use in forming a subcutaneous anatomical tunnel for implantation of a vascular graft in a patient is shown in FIGS. 1-3. The tunnel forming apparatus, also referred to herein as a tunneling device, comprises a tunneling instrument 100 including a proximal handle 102 and a distal tip assembly 50.

An arteriovenous graft suitable for use in this application is described in commonly owned U.S. Pat. No. 9,585,998, the contents of which are hereby incorporated by reference in their entirety. It is understood that the tunnel forming apparatus is also capable of use with other vascular grafts as well as a natural tissue graft or fistula.

Figure 4:
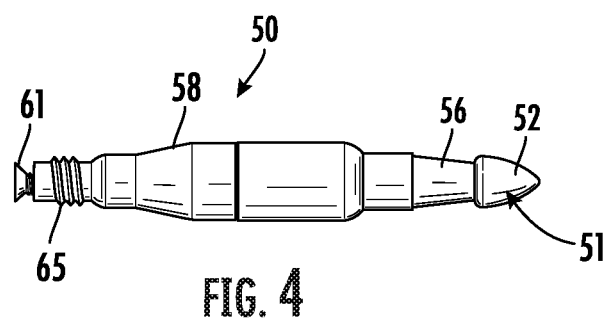
FIG. 4 is a side elevation view of the tip assembly as shown in FIGS. 1-3.
Figure 5:
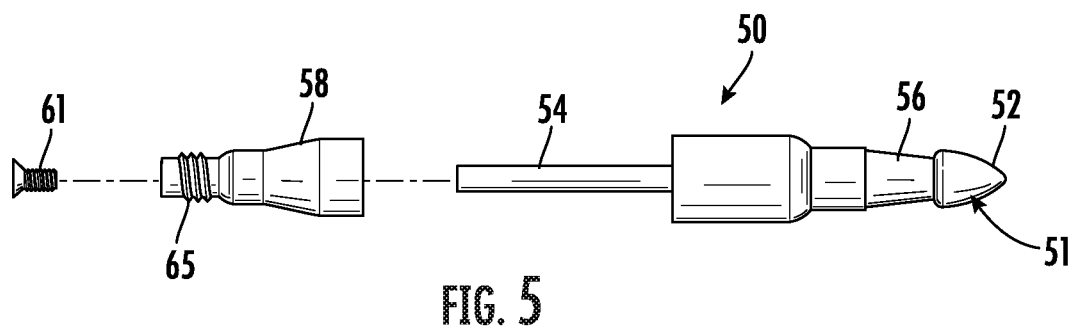
FIG. 5 is an exploded side elevation view of the tip assembly as shown in FIG. 4.

An embodiment of the tip assembly 50 is shown in FIGS. 4 and 5. The tip assembly 50 comprises a tip 51 and a swivel connector 58. The tip 51 and the swivel connector 58 may be constructed of stainless steel, but one of ordinary skill in the art will recognize that other materials may be suitable to connect an arteriovenous graft to the tunneling device. One such example of an alternative material is a plastic, such as a hard plastic.

Figure 6:
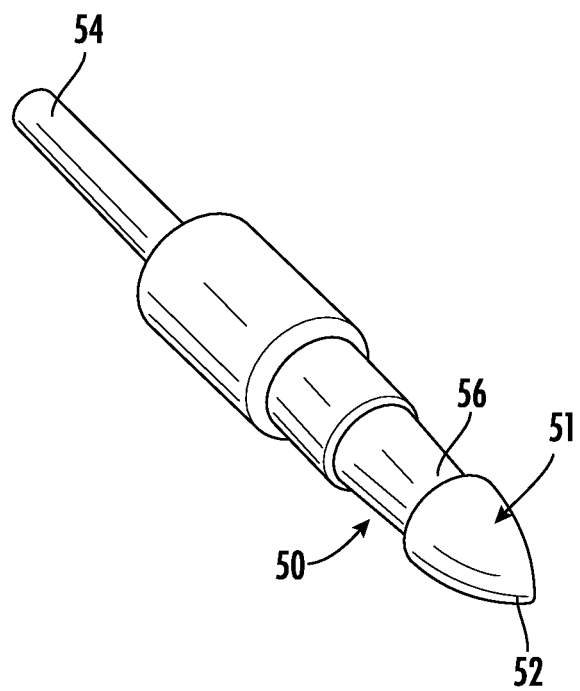
FIG. 6 is a distal end perspective view of an embodiment of a tip for use with the tip assembly as shown in FIG. 4.
Figure 7:
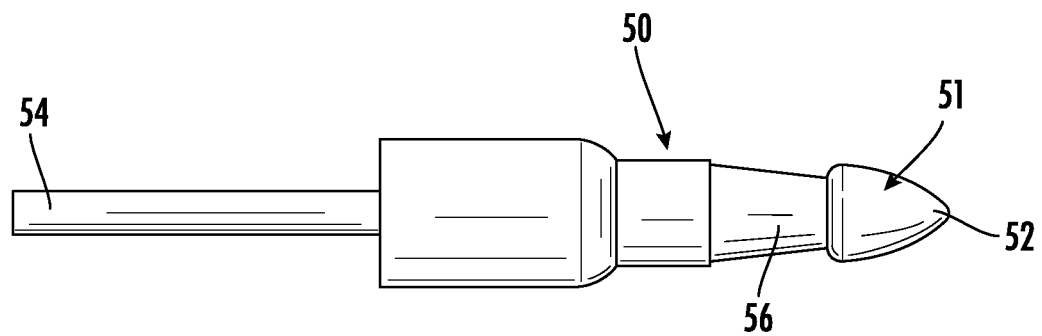
FIG. 7 is a side elevation view of the tip as shown in FIG. 6.
Figure 8:
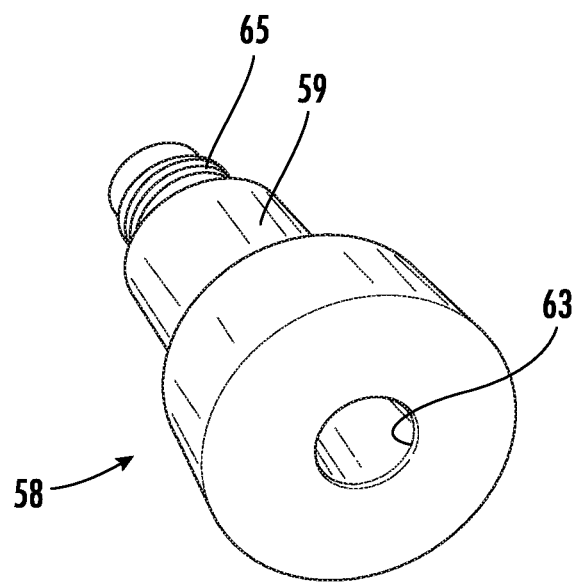
FIGS. 8 and 9 are distal and proximal end perspective views of an embodiment of a swivel connector for use with the tip assembly as shown in FIG. 4.
Figure 9:
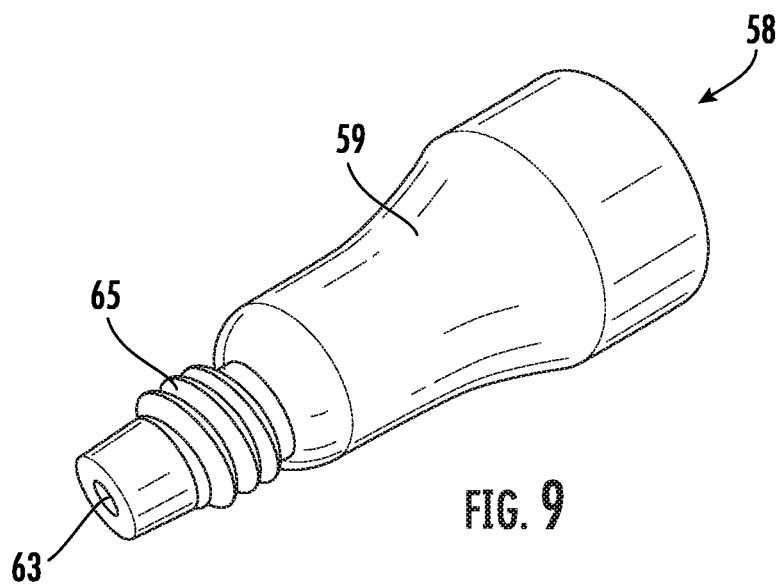

Referring to FIGS. 6 and 7, the tip 51 includes a bullet shaped distal end 52 and a longitudinally extending proximal end coupler 54. The swivel connector 58 comprises a bell-shaped ferrule 59 defining a central axial channel 63 for rotatably receiving the coupler 54 (FIGS. 8 and 9). The proximal end of the coupler 54 defines an internally threaded axial opening so that the ferrule 59 may be secured to the coupler 54 by a screw 61 for an axially rotatable swivel connection.

The proximal end of the ferrule 59 is externally threaded 65 for securing the tip assembly 50, and associated vascular graft, to the internally threaded distal end of the tunneling instrument 100. When assembled, the swivel connector 58 is rotatable about its longitudinal axis on the coupler 54 allowing the tip assembly 50 to be threaded into the tunneling instrument 100 without rotating a connected graft or a graft covered by a sheath. Other conventional methods of fastening the swivel connector 58 to the tunneling instrument 100 include snap-on or clip-on techniques that allow the ferrule 59 to snap or clip into a tunneling instrument. These and other fastening techniques are contemplated to be within the scope of the invention.

Figure 10:
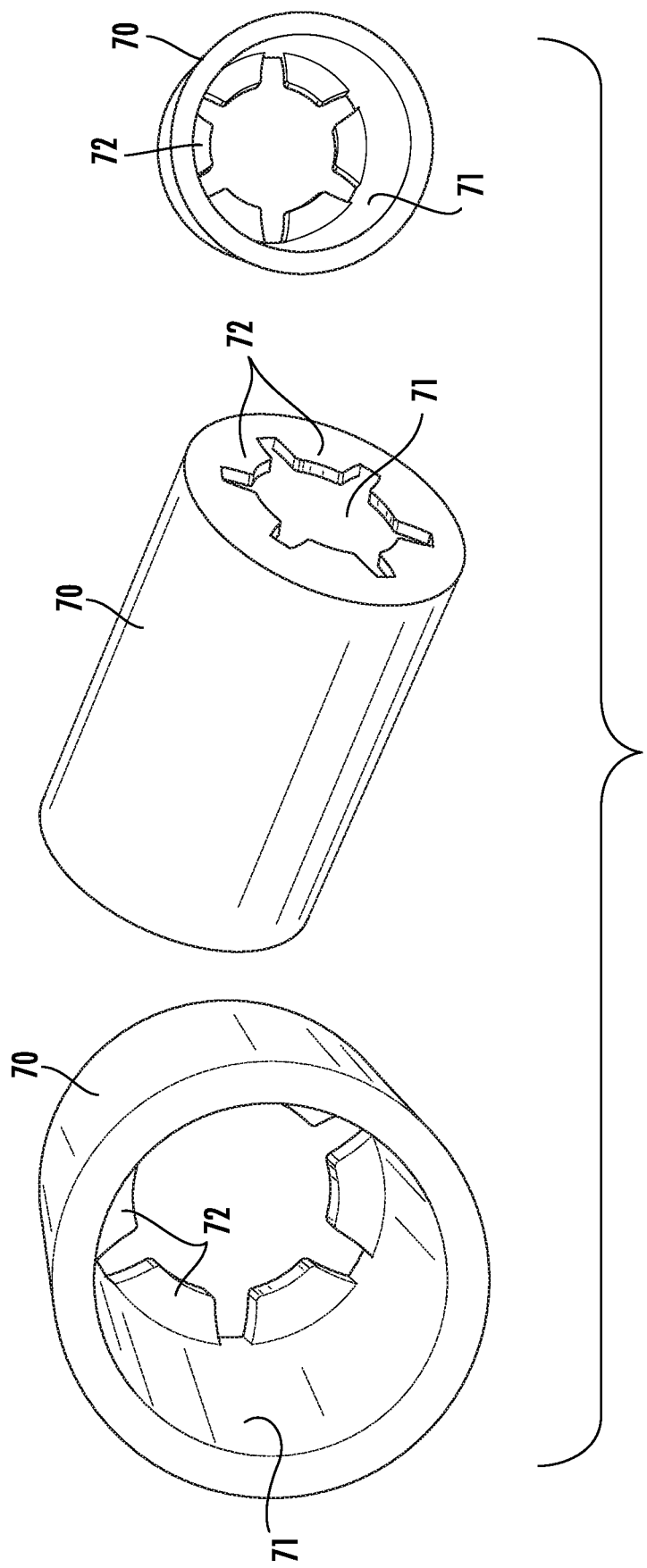
FIG. 10 is a front, side and rear perspective views of an embodiment of a graft clip for use in the tip assembly shown in FIG. 4.
Figure 11:
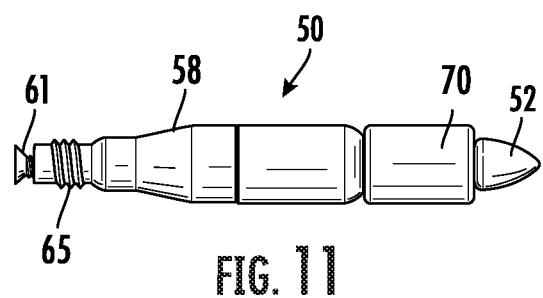
FIG. 11 is a side elevation view of the tip assembly and graft clip as shown in FIG. 10.
Figure 12:
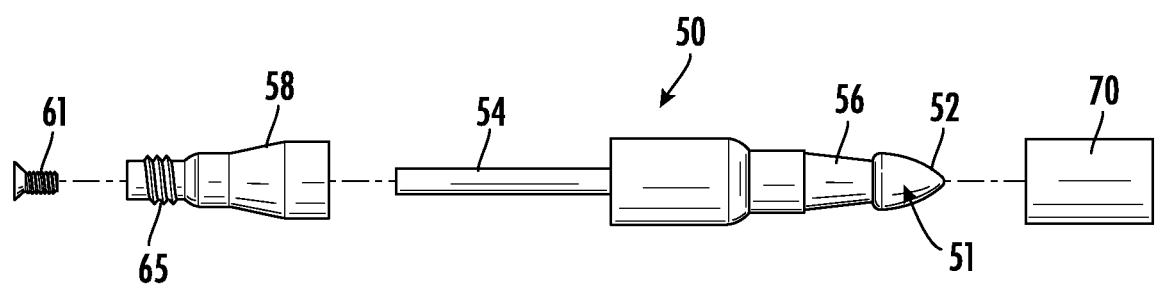
FIG. 12 is an exploded side perspective view of the tip and graft clip as shown in FIG. 11.
Figure 13:
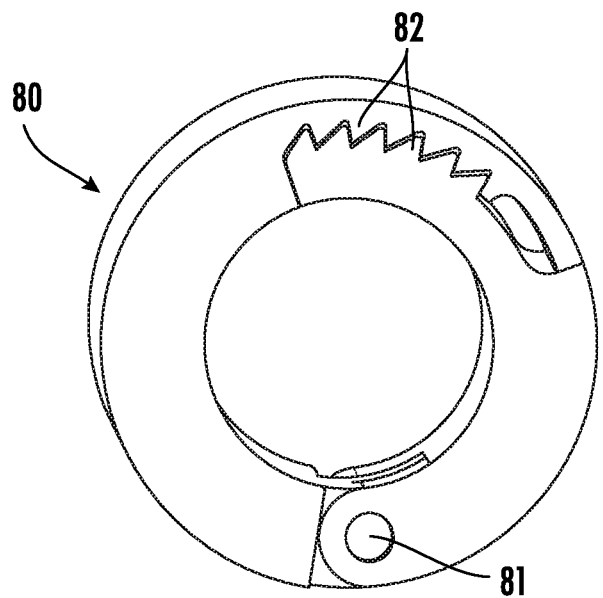
FIG. 13 is a front perspective view of another embodiment of a graft clip in a first closed position for use with the tip assembly as shown in FIG. 4.
Figure 14:
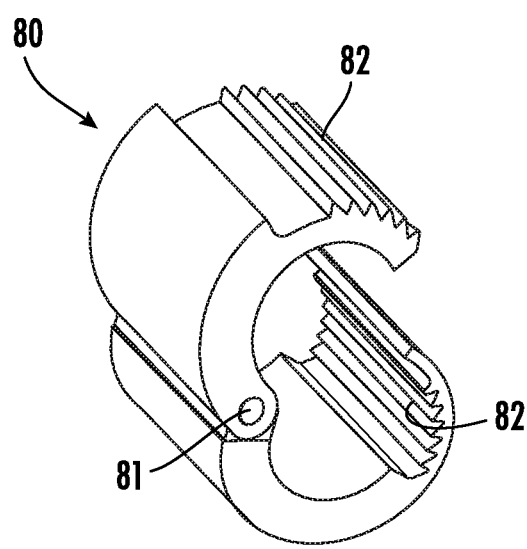
FIG. 14 is a front perspective view of the graft clip as shown in FIG. 13 with the graft clip in a second open position.
Figure 15:
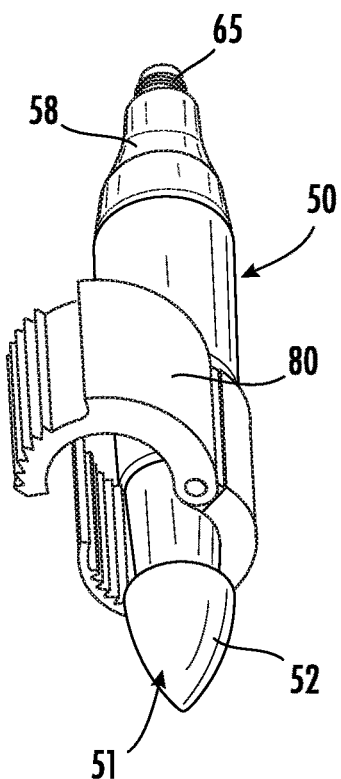
FIG. 15 is a front perspective view of the graft clip as shown in FIG. 14 with the graft clip in the open position on the tip assembly as shown in FIG. 4.
Figure 16:
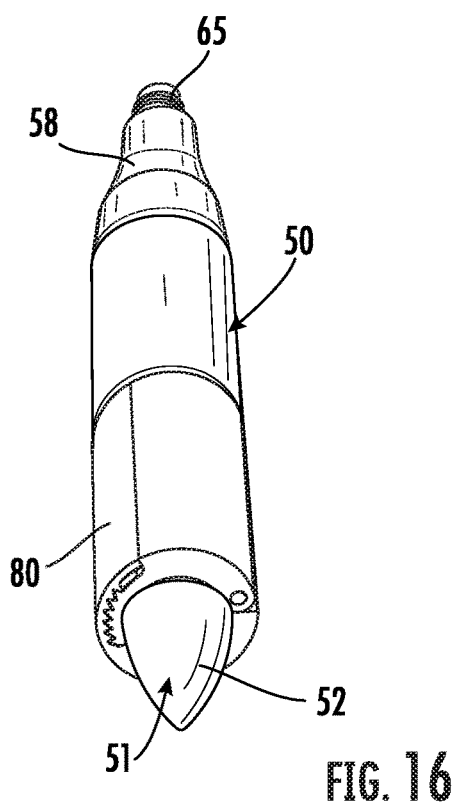
FIG. 16 is a front perspective view of the graft clip as shown in FIG. 13 with the graft clip in a second closed position on the tip assembly.

A fastening clip may be used to couple a vascular graft 10, or the graft and a sheath 20, to the tip assembly 50 such that the sheath is attached to and encloses at least the proximal end and a portion of the length of the vascular graft. In one embodiment shown in FIG. 10 and generally designated at 70, the fastening clip comprises a hollow cylindrical cap 70. A distal end of the cap 70 includes a plurality of fingers 72 extending radially inwardly into the passage 71 defined by the cap. The cap 70 is configured to receive and enclose a portion of the proximal end of the arteriovenous graft. Referring to FIGS. 11 and 12, the tip 51 includes a smaller diameter portion spaced from the distal bullet-shaped end 52 and forming a peripheral annular groove 56. The annular groove 56 is configured to receive the proximal end of the graft, and sheath if present, enclosed by the cap 70. In use, the graft and sheath may be coupled to the tip 51 by passing the graft and sheath through the cap 70. The graft and sheath are then secured to the tip 51 by slipping the cap 70 with the graft and sheath over the distal end 52 of the tip 51 and axially along the tip 51 until the fingers 72 seat in the groove 56. In this configuration, the proximal end of the graft and sheath are enclosed within the cap 70 and securely within the groove 56 for fixedly positioning the graft and sheath therein.

Figure 17:
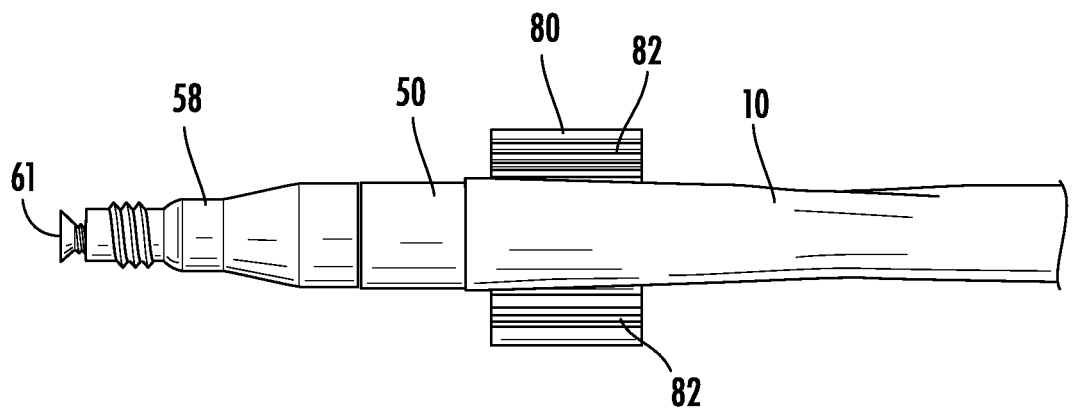
FIG. 17 is a side perspective view of the graft clip as shown in FIG. 14 with the graft clip in the open position on the tip assembly as shown in FIG. 4 and surrounding a proximal end of an AVG.
Figure 18:
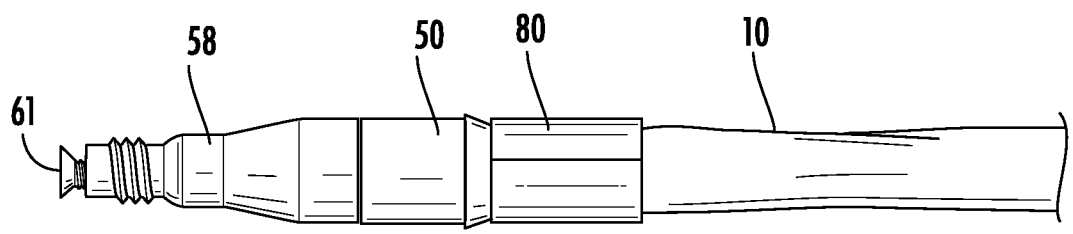
FIG. 18 is a side perspective view of the graft clip as shown in FIG. 13 with the graft clip in a second closed position on the tip assembly over the proximal end of the AVG.
Figure 22:
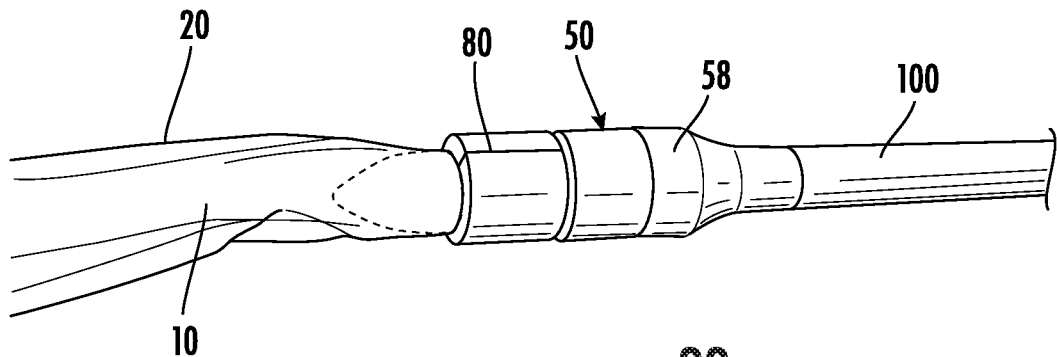
FIG. 22 is a close-up of the perspective view of the sheath and arteriovenous graft connected to the tip assembly and tunneling instrument as shown in FIG. 21.
Figure 21:
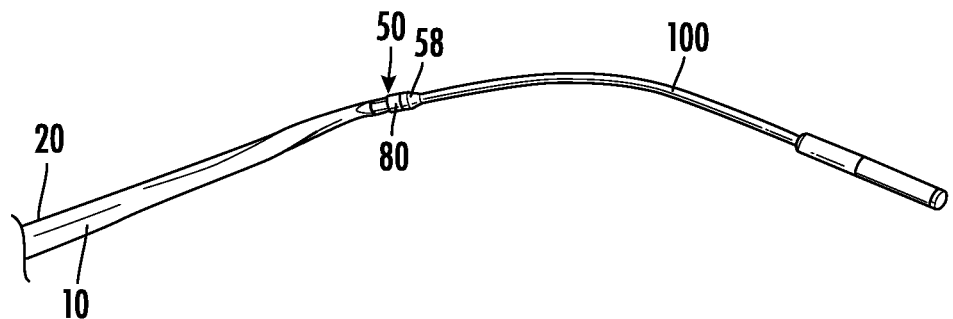
FIG. 21 is a perspective view of a sheath surrounding at least a substantial portion of an arteriovenous graft and secured with the AVG to the tip assembly and tunneling instrument as shown in FIG. 1 using the clip as shown in FIG. 13.

Another embodiment of a fastening element for securing an arteriovenous graft, or the vascular graft and a sheath, to the tip assembly 50 is shown in FIGS. 13-16 and generally designated at 80. In this embodiment, the fastening element comprises a lock ring 80 mounted around a proximal end of the graft, or graft and sheath, for securing the graft in the groove 56 and preventing axial movement of the graft relative to the tip assembly 50. More particularly, the lock ring 80 may be coupled to the tip 51 by crimping about a pivot pin 81 such that teeth 82 on opposed surfaces of the free ends of the lock ring 80 engage for enclosing the graft and sheath within the groove 56 and fixedly positioning the graft, or graft and sheath therein (FIGS. 17 and 18). This arrangement provides for coupling of a tunneling instrument 100 to an arteriovenous graft 10 by a compressive force on the graft for subcutaneously deploying the graft 10 in a patient. The arteriovenous graft 10 may be surrounded by a sheath 20 for drawing both into the subcutaneous tissue cavity in the patient. The sheath 20 is secured to the tip assembly 50 and surrounds at least a substantial portion of the arteriovenous graft as shown in FIGS. 21 and 22.

Figure 19:
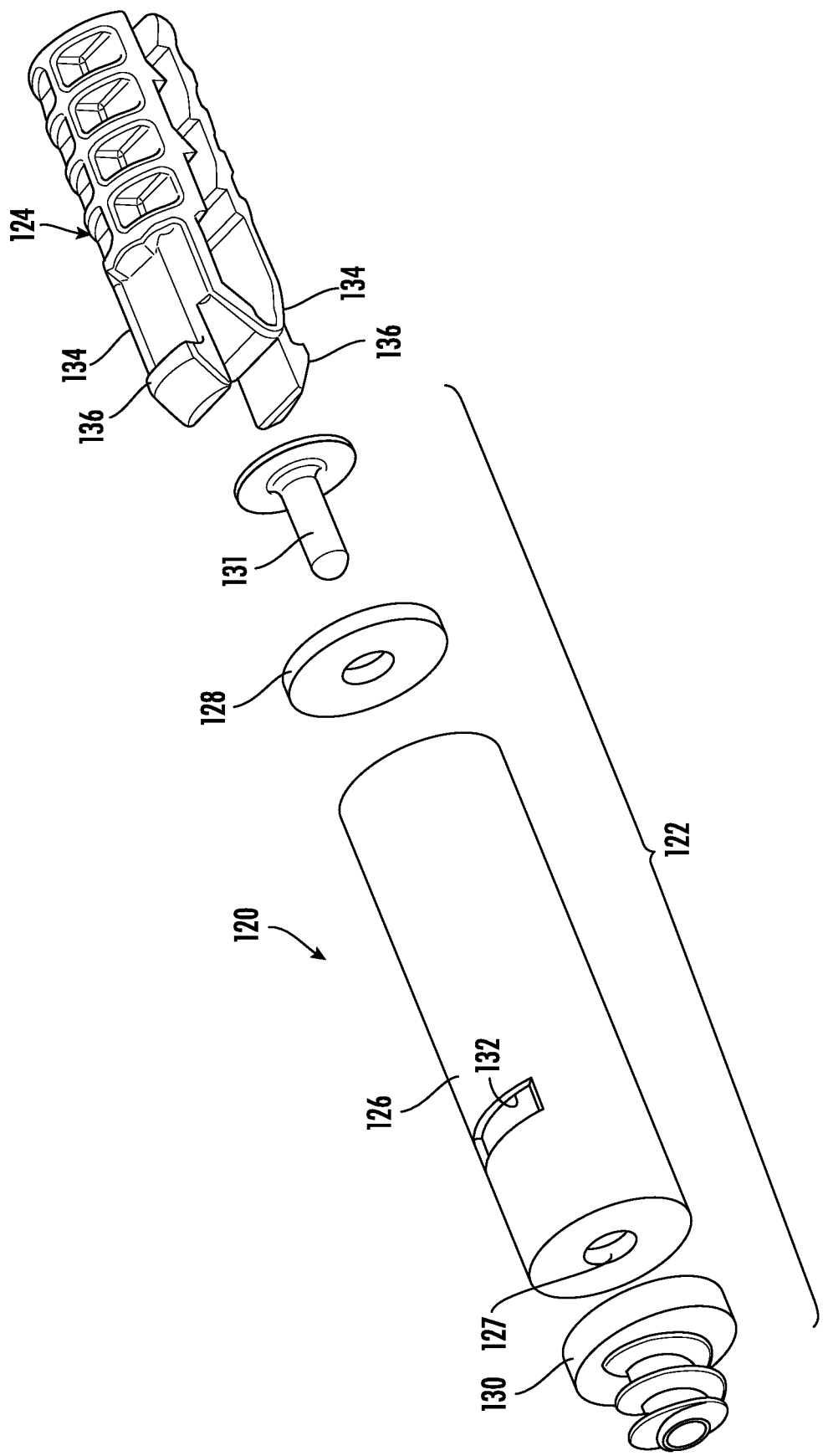
FIG. 19 is an exploded perspective view of an embodiment of a coupler for connecting a proximal end of an arteriovenous graft to a distal end of a tunneling device.

FIG. 19 shows yet another embodiment of a fastening element for securing an arteriovenous graft, or the graft and a sheath, to a tunneling instrument 100 and is generally designated at 120. In this embodiment, the tip assembly 50 is removed and the fastening element is secured directly to the distal end of the tunneling instrument 100. The fastening element comprises a coupler 120 including a socket 122 and a clip 124 to be connected between a distal end of the tunneling device and a proximal end of the graft. The socket 122 includes a hollow cylindrical sleeve 126, a washer 128 and a threaded proximal plug 130 for threadably securing the sleeve 126 to an internally threaded end of the tunneling device 100. The plug 130 is connected to the proximal end of the sleeve 126 via an opening 127 in the sleeve with a screw 131 and washer 128 there between. This arrangement allows the plug 130 to rotate relative to the sleeve 126. The sleeve 126 has opposed partially circumferential slots 132 spaced intermediately along the length of the sleeve 126. The proximal end of the clip 124 includes a pair of axial flexible arms 134. Each of the arms 134 has a radially outwardly extending shoulder 136. The remainder of the clip 124 distally of the arms 134 is generally circular in cross-section.

In use, the plug 130 and connected sleeve of the socket 122 is threaded onto the distal end of the tunneling instrument 100. The proximal end of the graft is pushed over the distal portion of the clip 124 for securing the graft to the clip. The clip 124 and graft are then pushed into the distal open end of the sleeve 126. This causes the arms 134 to compress inwardly together until the shoulders 136 reach the slots 132 at which point the arms 134 spring outwardly as the shoulders 136 enter the slots 132. This fastens the socket 122 and clip 124 together along with the connected tunneling device and graft. The user can now pull the graft into the subcutaneous tunnel previously formed by the tunneling instrument 100.

Figure 20:
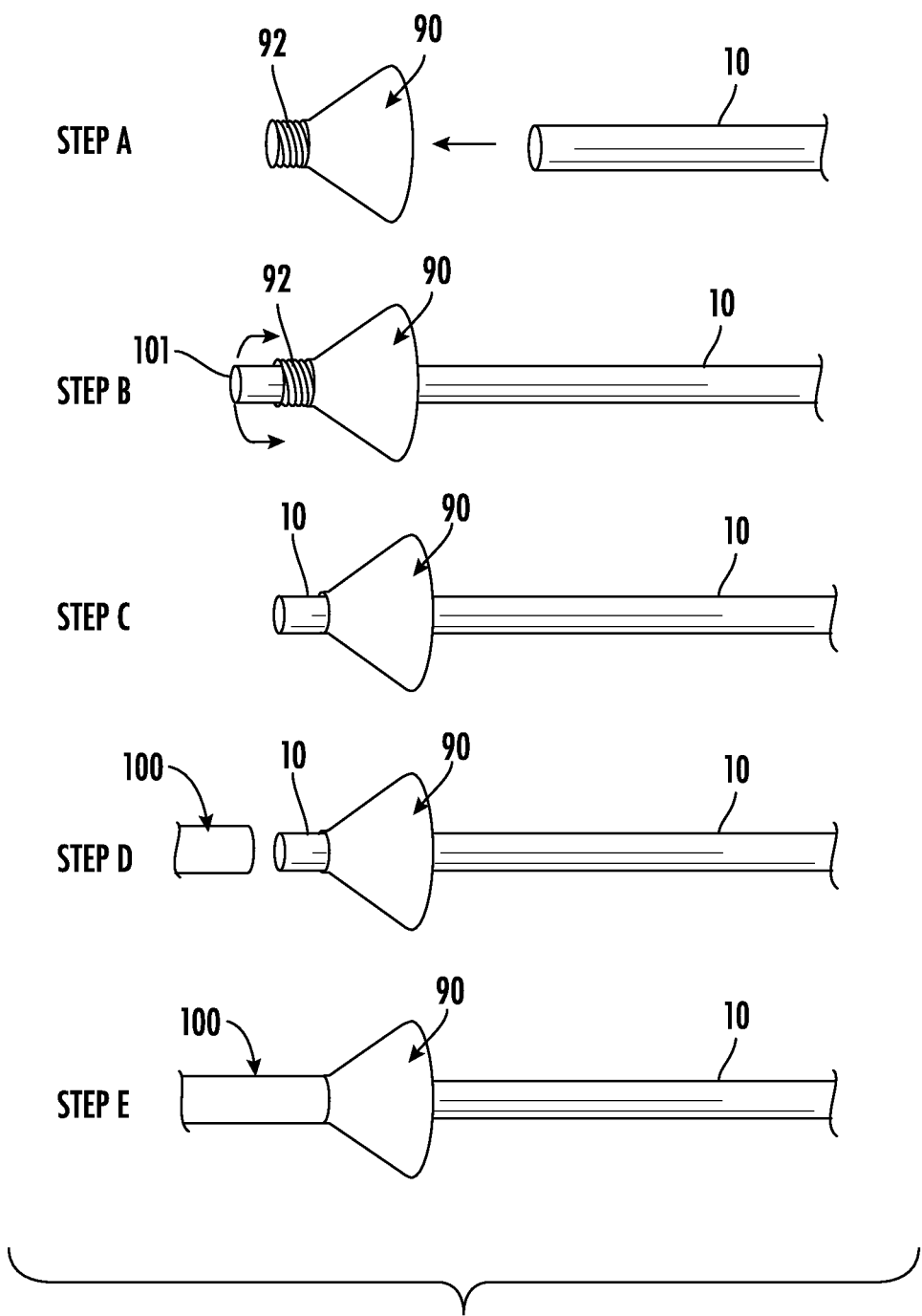
FIG. 20 is a side perspective views of another embodiment of a tunneling device including a frustoconical hood showing steps for use as a coupler for connecting a proximal end of an arteriovenous graft to a distal end of a tunneling device.

Referring now to FIG. 20, another embodiment of a fastening element for securing an arteriovenous graft, or the graft and a sheath, directly to a tunneling instrument 100 is shown and generally designated at 90. The fastening element comprises a frustoconical cup 90 has an axial opening through a small diameter externally threaded proximal end 92 configured for receiving the graft (Step A). The proximal end of the graft passes through the end 92 of the cup 90 (Step B) and is then folded back over the threads (Step C). The proximal end 92 of the cup 90 is threaded into the distal end of the tunneling instrument 100 (Step D), such that the large diameter open end of the cup 90 is facing distally away from the tunneling device 100 (Step E).

In use, after the distal end of the tunneling instrument 100 emerges from the second distal incision, the proximal end of the vascular graft is pulled through the cup 90 and everted back over the periphery of the threaded end 92 of the cup 90 (Steps B and C). The cup 90 and graft are then threadably connected with the distal end of the tunneling device 100 for securing the end of the graft (Steps D and E). Once connected, the cup 90 is be pulled by the tunneling device 100 along with the graft through the anatomical subcutaneous path created by the tunneling device. The cup 90 assists in the passage of the graft into the body by causing the outward deflection of surrounding tissue upon contacting the frustoconical cup 90. After the graft is pulled through the tissue tunnel, the cup is removed prior to anastomosis of the graft.

It is understood that other means for connecting the end of the cone 90 to the tunneling device 92 which do not require threads are suitable.

Figure 23A:
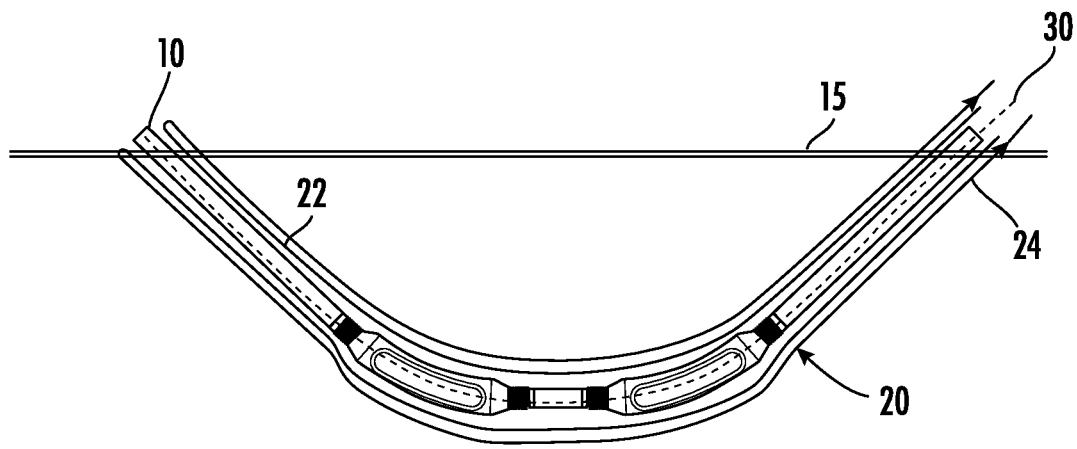
FIGS. 23A-23C are schematic views of an arteriovenous graft enclosed within an embodiment of a removable sheath with a proximal end of the combined graft and sheath attached to the tip assembly on a tunneling instrument.
Figure 23B:
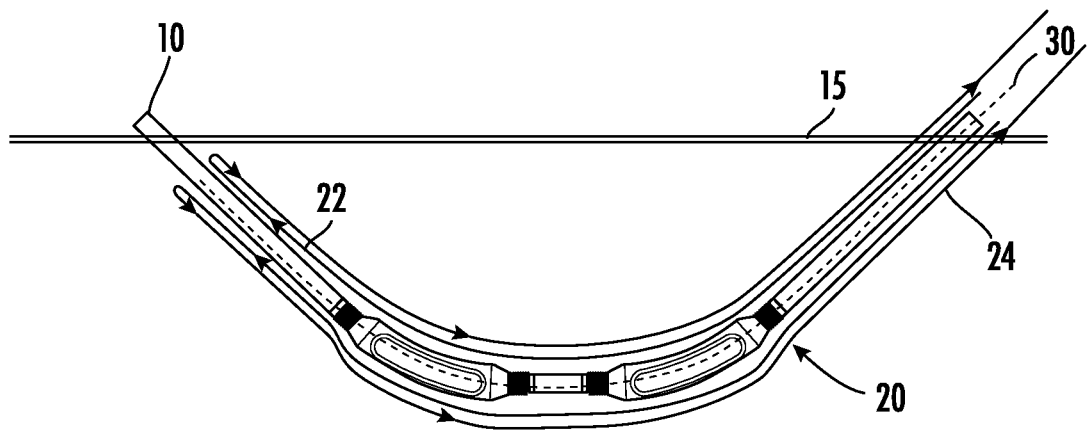
Figure 23C:
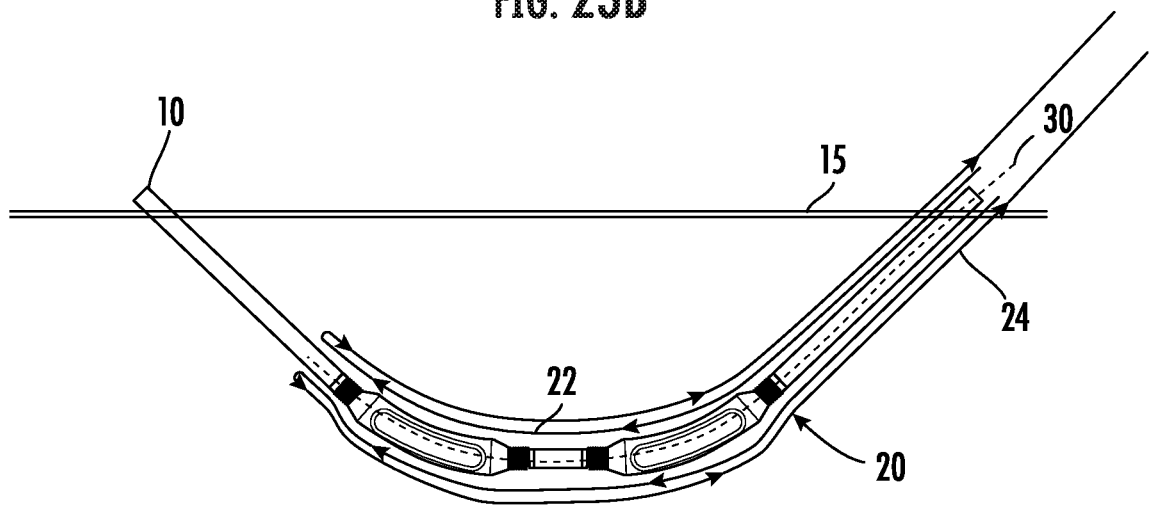

Referring to FIGS. 23A-23C, a system is shown for implanting an arteriovenous graft (AVG) 10 further comprising a tubular sheath 20 positioned over and enclosing at least a substantial portion of the outer surface of the graft during the implantation procedure. Following implantation of the arteriovenous graft 10, the sheath 20 is configured to roll along the graft 10 upon application of a pulling force along the longitudinal axis of the sheath 10 to extract the sheath.

The sheath 20 comprises a tubular structure that is dimensioned in diameter and length to cover at least a substantial portion of the outer surface of the AVG 10. The sheath 20 can be constructed from any smooth, flexible and compressive biocompatible material. Suitable material can be porous, non-porous, permeable, or impermeable. Examples of such materials include, but are not limited to, silk, silicone, fluoropolymers such as expanded polytetrafluoroethylene (ePTFE), high density polyethylene (HDPE), and other polymers such as polyesters and polyimides. Various desired configurations may be achieved by varying film materials and characteristics, such as thickness and width. The sheath 20 may be extruded, for example, directly over a lead body or as a pre-manufactured item subsequently attached to a lead. The sheath 20 allows for easier insertion of the graft 10 through the tunneled tissue path due to the unrestricted and flexible nature of the compressible outer surface of the sheath. The sheath 20 may be constructed of a material that does not excessively flex, so that the sheath 20 absorbs the tensile force imparted during tunneling as opposed to the graft 10. This will help to prevent damage to the graft 10, which may reduce graft stretching and subsequent graft weeping and seroma formation, and damage that may allow the graft to kink.

In the embodiment of the implantation system shown in FIGS. 23A-23C, the sheath 20 is doubled over on itself such that the amount of material used to make the sheath will be at least double the length desired to cover the AVG. The sheath 20 in this embodiment has a "double walled" construction. An inner portion 22 of the sheath 20 extends from a position proximal of the AVG 10 radially over and axially along the AVG to a position distal of the AVG where the inner portion 22 is folded back to provide an outer portion 24. The outer portion 24 extends radially over the inner portion 22 and to a position proximal of the AVG 10. When the sheath 20 is extracted by a rolling action, the sheath 20 will slide over itself thus reducing the force necessary to extract the sheath. It is understood, however, that an embodiment of the sheath 20 may have a sufficiently low coefficient of friction that the sheath can be removed from the tunnel by pulling the sheath from the tunnel and not a rolling motion.

As shown in FIGS. 23A-23C, the sheath 20 has perforations 30 disposed along the longitudinal axis of the sheath. The perforations 30 are generally oriented linearly in diametrically opposed positions along the length of the sheath 20. The perforations 30 allow the sheath to tear at the perforations upon rolling as the sheath 20 is extracted. In another embodiment, the sheath 20 may comprise weakened areas of material that will tear as the sheath is extracted. During retraction, the sheath 20 is drawn axially proximally relative to the AVG 10 to retract the sheath from over the AVG. The pulling force retracts the sheath 20 from the distal end and progressively proximally with the outer sheath 24 moving over the inner sheath 22 in a rolling manner.

Figure 24A:
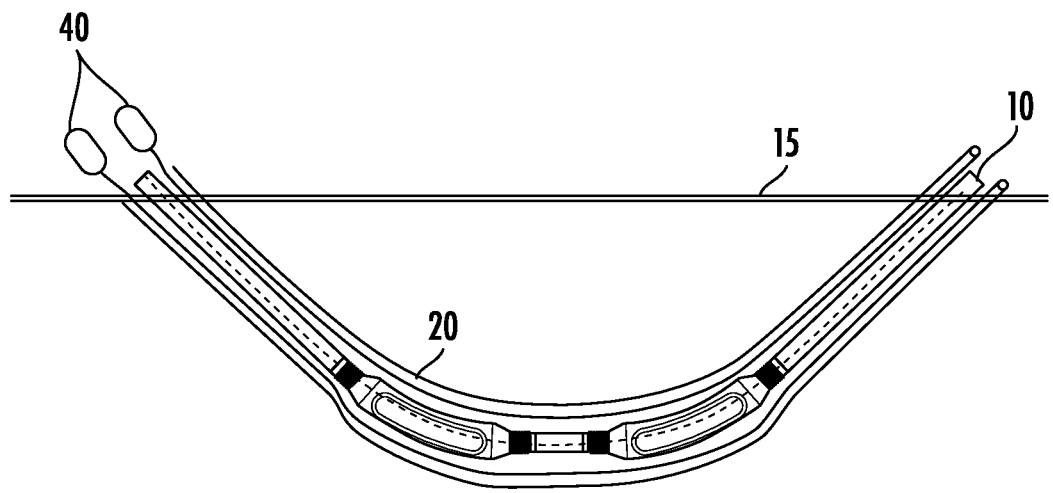
FIGS. 24A and 24B are schematic views of an arteriovenous graft enclosed within another embodiment of a removable sheath with a proximal end of the combined graft and sheath attached to the tip assembly on a tunneling instrument.
Figure 24B:
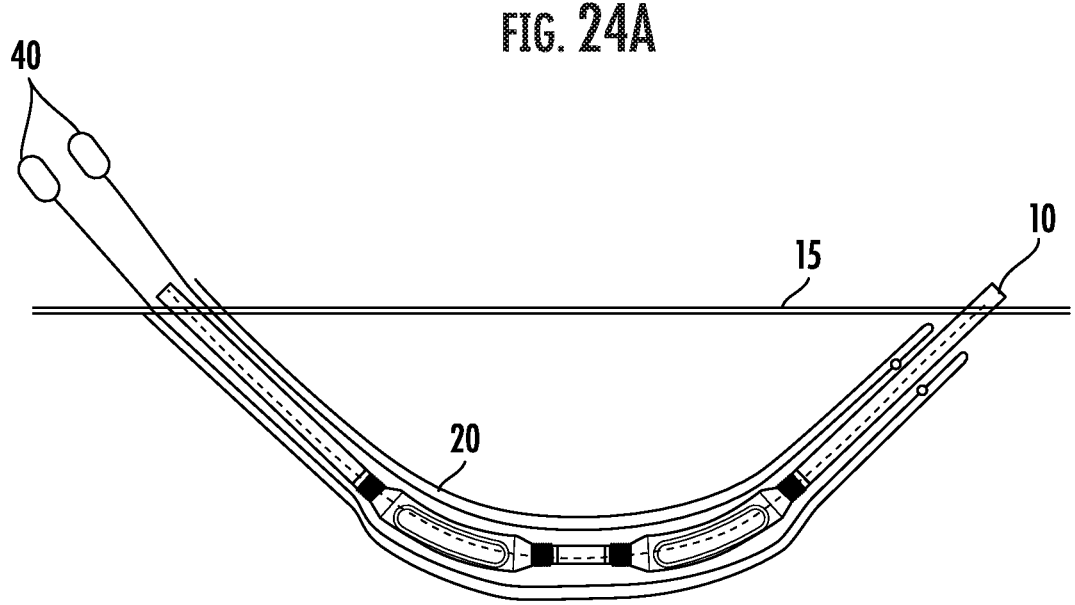

Referring to the embodiment shown in FIGS. 24A and 24B, the sheath 20 is drawn axially proximally relative to the AVG 10 to retract the sheath from over the arteriovenous graft by the pulling force provided by a moveable tether 40. The tether 40 extends axially from adjacent a proximal end of the arteriovenous graft to an opposite distal end of the graft where the tether 40 joins the outer portion 24 of the sheath 20 at or beyond the distal end of the graft 10. The tether 40 extends sufficiently proximally externally to the first incision so that it can be pulled upon for retracting the sheath 20. The tether 40 is pulled upon to retract the sheath 20 from the distal end and progressively proximally with the outer sheath 24 moving over the inner sheath 22 in a rolling manner. The tether 40 may be a plastic thread or a metal wire.

Figure 25A:
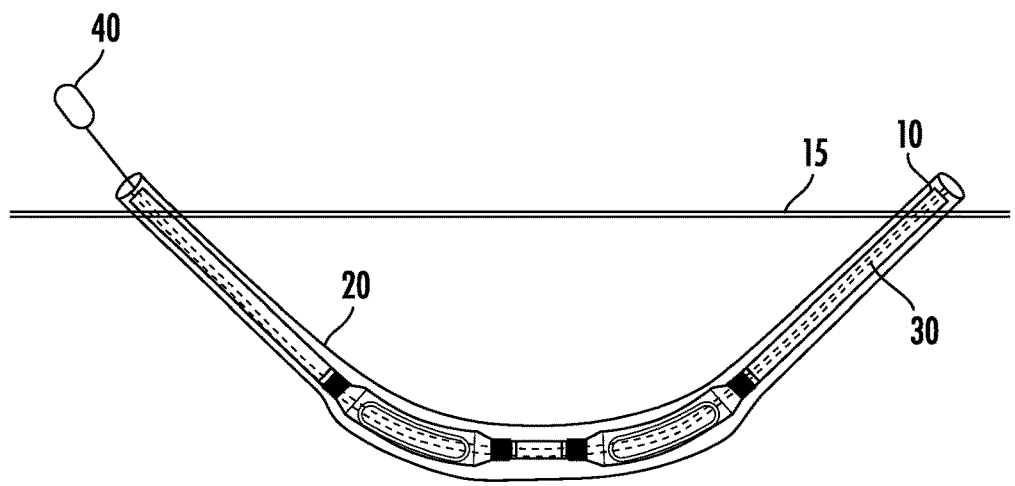
FIGS. 25A-25C are schematic views of an arteriovenous graft enclosed within a third embodiment of a removable sheath with a proximal end of the combined graft and sheath attached to the tip assembly on a tunneling instrument.
Figure 25B:
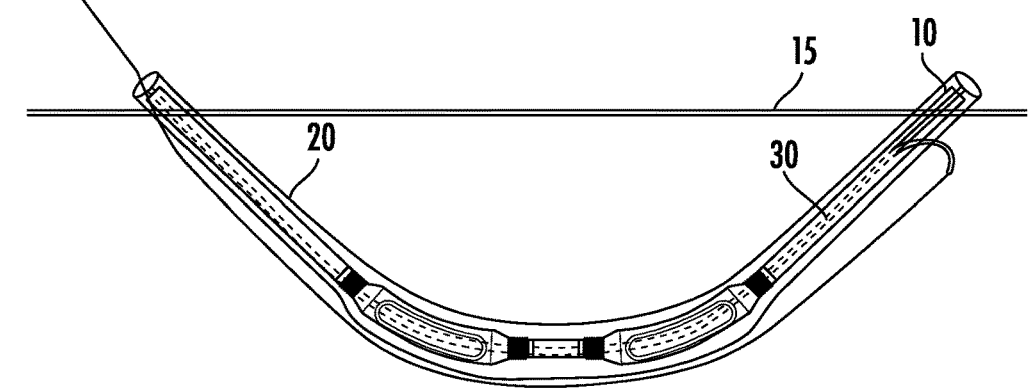
Figure 25C:
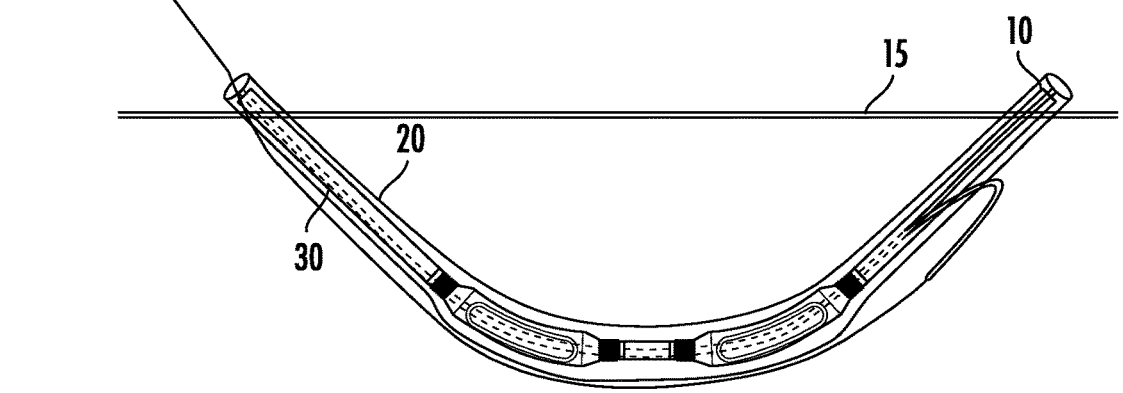

Referring to the embodiment shown in FIGS. 25A-25C, the sheath 20 is a single layer having perforations 30 disposed along the longitudinal axis of the sheath. The perforations 30 are generally oriented linearly in close parallel relation along the length of the sheath 20. The perforations 30 allow the sheath to tear at the perforations upon rolling as the sheath 20 is extracted. The tether 40 extends axially from adjacent a proximal end of the arteriovenous graft to an opposite distal end of the graft where the tether 40 joins the sheath 20 between the perforations 30 at or beyond the distal end of the graft 10. The tether 40 extends sufficiently proximally externally to the first incision so that it can be pulled upon for retracting the sheath 20. The tether 40 is pulled upon to retract the strip of the sheath 20 between the perforations 30.

When the arteriovenous is subcutaneously located as desired, the tether 40 or the sheath 20 itself is pulled. FIGS. 23B, 24B and 25B show the pulling force as depicted by arrows. The pulling force moves the sheath 20 proximally which, in one embodiment, causes the outer sheath 24 to slide over the inner sheath 22. As the sheath 20 rolls proximally, the sheath is torn at the perforations 30. As the pulling force continues, the sheath 20 will continue to move proximally until the sheath 20 is extracted from the first incision and the arteriovenous graft 10 is uncovered.

The sheath 20 may be coated on the outside surface with a lubricious substance to provide a low coefficient of friction, aiding movement of the sheath 20 and graft 10 through tissue when pulled by a tunneling instrument. This will minimize tissue drag and tissue trauma during insertion of the arteriovenous graft 10 or removal of the sheath 20 after implantation. The lubricant will also allow the sheath 20 to slide smoothly across itself. Solid lubricants (i.e. graphite, waxes, silicone), fluid lubricants (i.e. hydrocarbon oils, silicone oils), gels (i.e. hydrogel) or any other biocompatible material known in the art may be used. In one embodiment, the sheath 20 can be coated or wetted immediately before implantation by the user. In another embodiment, the invention comprises a kit comprising a sheath and a wetting agent for wetting the sheath 20. In another embodiment, the invention comprises a kit comprising a sheath 20, an arteriovenous graft 10 and a wetting agent for wetting the sheath.

The sheath 20 may be attached to at least the distal end of the arteriovenous graft by mechanical, rail or interference fit, mechanical structures, heat bonding or by a biocompatible adhesive or other securing means. Example adhesives are thermoplastic fluoropolymers, such as fluorinated ethylene propylene (FEP). The sheath may also be attached to the arteriovenous graft following its manufacture as a separate component.

The system and method for implanting the arteriovenous graft, including a sheath enclosing the graft during implantation, have many advantages, including atraumatic implantation of an arteriovenous graft and subsequent extraction of the associated sheath. The sheath provides a flexible, compressible outer surface for the graft that may allow for easier insertion of the graft into the tissue cavity with less trauma, less friction, and less drag during placement. Thus, the system and method described herein reduce damaging forces to surrounding tissues associated with the implant procedure and minimize the resultant trauma to this tissue and its healing response. Due to the smoothness and collapsible low profile of the sheath, the tunneling procedure may be faster and easier to use, in addition to being less traumatic to tissue.

Figure 26:
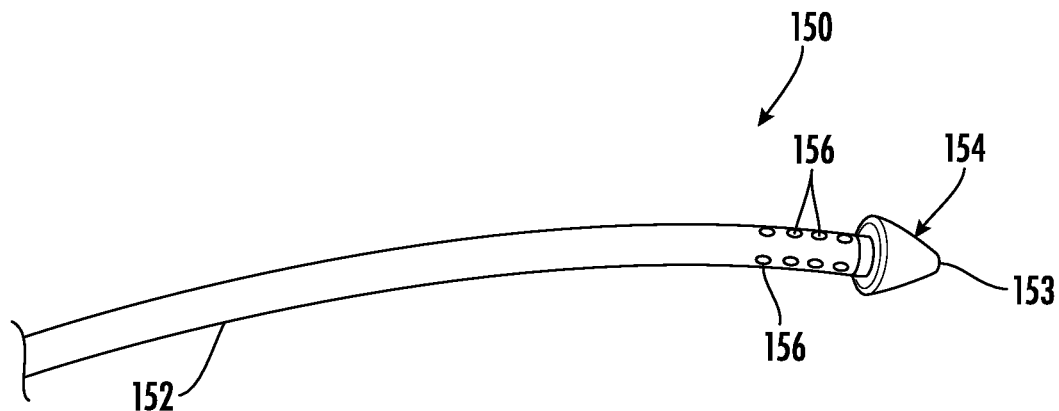
FIG. 26 is a side perspective view of another embodiment of a tip assembly and tunneling instrument for use in forming a subcutaneous anatomical tunnel for implantation of a vascular graft.

FIG. 26 shows an embodiment of a tunneling instrument generally designated at 150. The shaft 152 defines an axial opening extending through its entire length. The distal end of the shaft 152 has a plurality of holes 156 in fluid communication with the axial opening through the shaft 152. This configuration allows infusion or aspiration of a fluid from a fluid source delivered through the shaft 152 to the tip 154. During advancement of the tunneling instrument 150 through the subcutaneous tissue, fluid can be infused from the fluid source and through the distal shaft holes 156. The infused fluid exits the shaft holes 156 adjacent to the distal end 153 of the tip 154 for lubricating the tissue passage. Examples of fluid for use in this application include, but are not limited to, phosphate-buffered saline, saline and buffered saline as well as gas.

Figure 27:
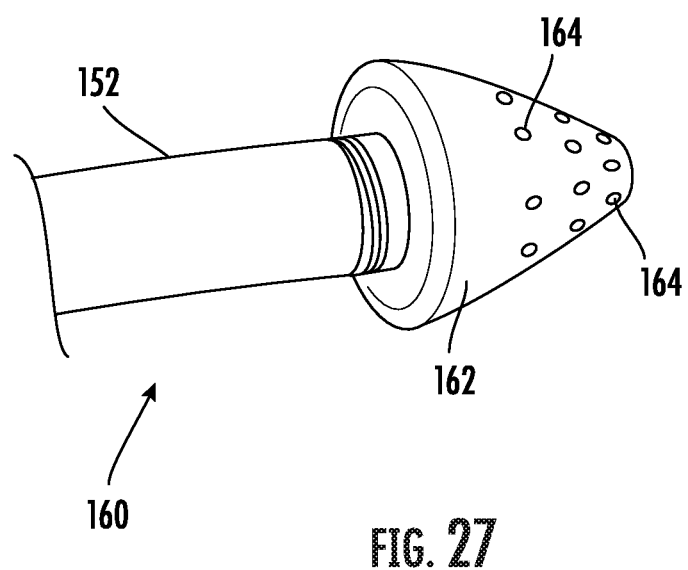
FIG. 27 is a side perspective view of a third embodiment of a tip assembly and tunneling instrument for use in forming a subcutaneous anatomical tunnel for implantation of a vascular graft.

Referring to FIG. 27, another embodiment of a tunneling instrument for delivering fluid is shown and generally designated at 160. In this embodiment, the tip 162 or nose section has a plurality of openings 164. When the tip 162 is fastened to the distal end of the shaft 152, the axial opening through the shaft is in fluid communication with the holes 164 in the tip 162. In use, the tunneling apparatus 160 delivers pressurized fluid, such as air, from a fluid source through the shaft 152 and through the holes 164 in the tip 162 during advancement of the tunneling apparatus 160 through subcutaneous tissue. The pressurized fluid exits the tip 162 in the direction of advancement of the tunneling apparatus 160 for aid in dissecting tissue during the tunneling procedure.

Figure 28:
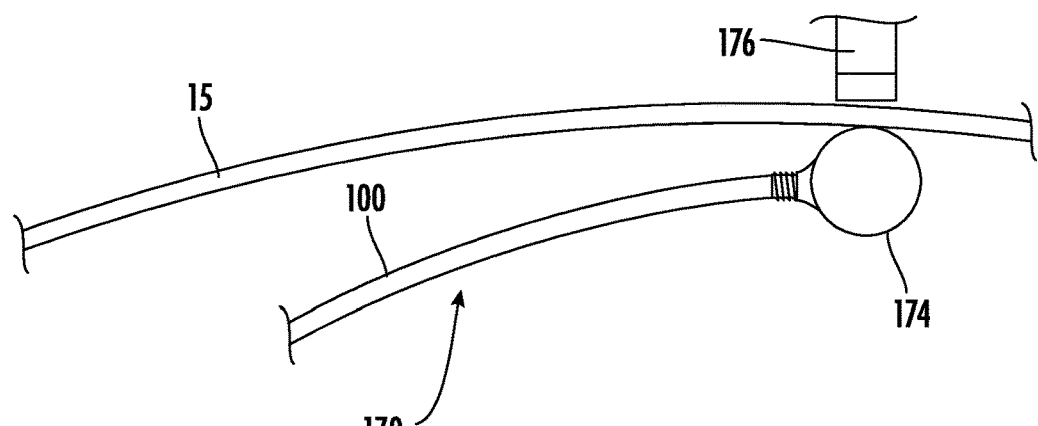
FIG. 28 is a side perspective view of a fourth embodiment of a tip assembly and tunneling instrument for use in forming a subcutaneous anatomical tunnel for implantation of a vascular graft including a magnetic tip portion and a wand.

Yet another embodiment of a tunneling apparatus is shown in FIG. 28 and generally designated at 170. The tunneling apparatus 170 comprises a rigid shaft 172 with a magnetic tip 174, or nose section, at a distal end 173 of the shaft. As with other tips described herein, the magnetic tip 174 has an elliptical or circular shape that facilitates the blunt dissection inherent in the tunneling procedure. As shown in FIG. 28, a magnetic wand 176 is provided for engaging the tip 174 across the skin 158 boundary. During the tunneling procedure, the tip 174 is advanced through the subcutaneous tissue by moving the wand 176 along the surface of the skin 178.

Figure 29:
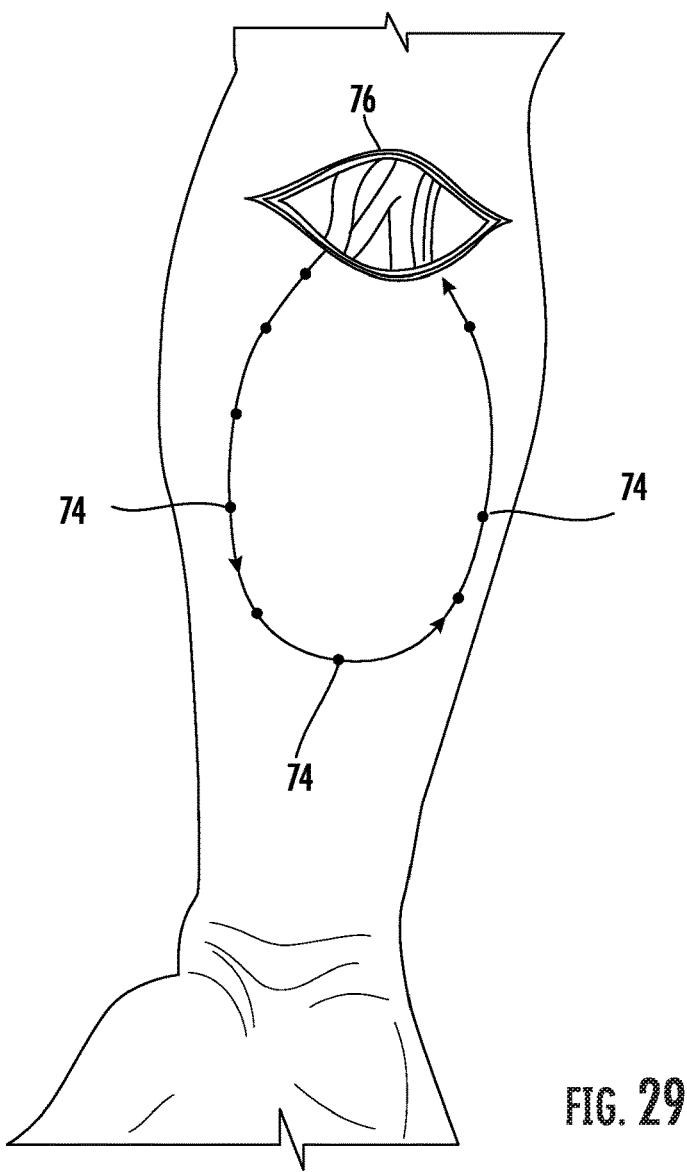
FIG. 29 is a schematic front elevation view of an embodiment of an apparatus for use in forming a subcutaneous anatomical tunnel for implantation of a vascular graft using a self-guided tunneling device.

An embodiment of a self-guiding tunneling apparatus is shown in FIG. 29. In this embodiment, markers 92 placed on the skin 94 of a patient indicate a predetermined path for the anatomical tunnel for placement of a vascular graft 10. The markers 92 identify proper placement of a tunneling device (not shown) beginning from an incision 96 into the body. The user follows the markers 92 in navigating the tunneling device through the body, thereby increasing the accuracy of the procedure by following well-established practices of guide wire navigation.

Figure 30:
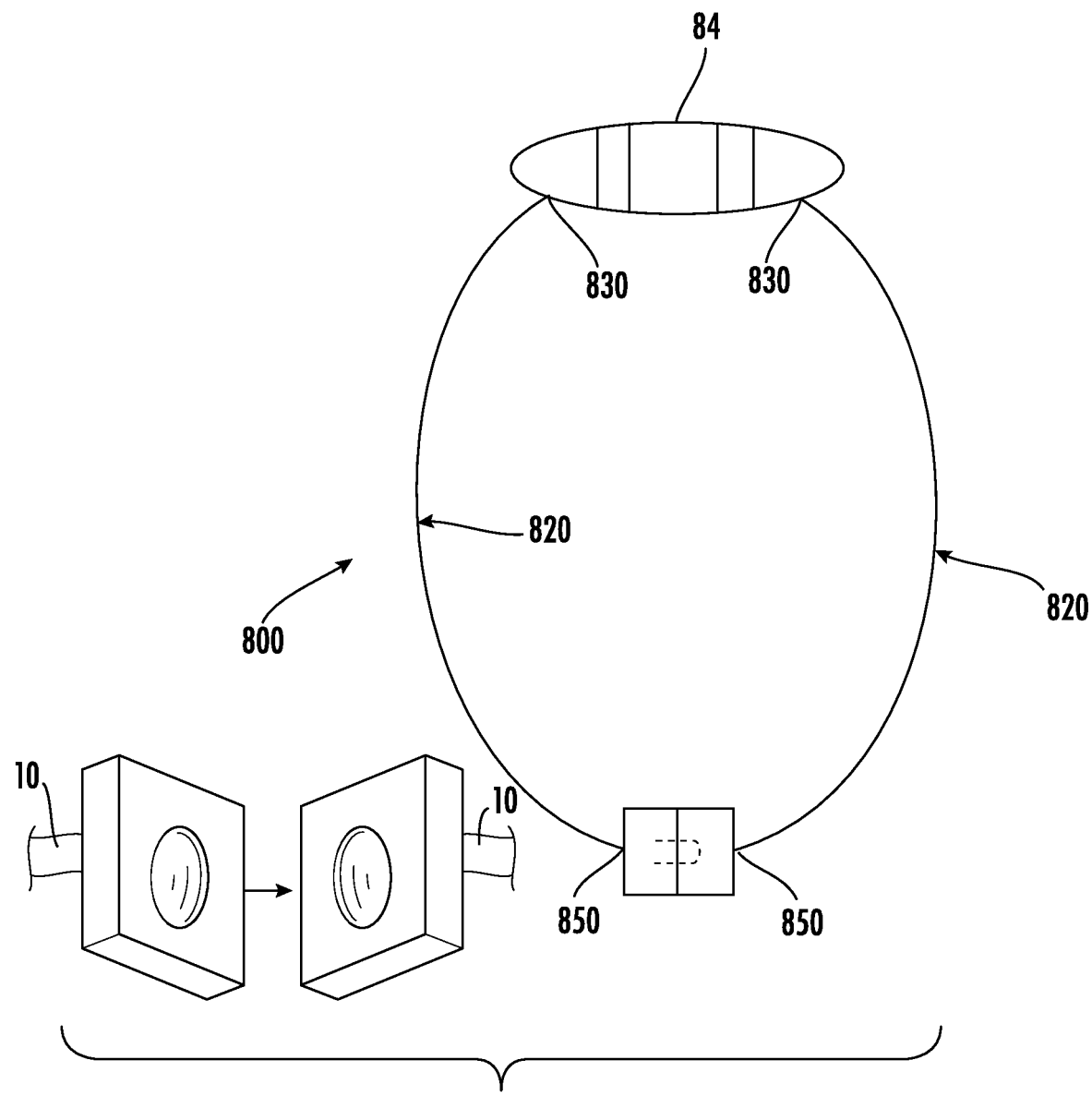
FIGS. 30 and 31 are schematic front elevation views of an embodiment of an apparatus for use in forming a subcutaneous anatomical tunnel for implantation of a loop vascular graft using two-piece tunneling device having a distal locking mechanism.
Figure 31:
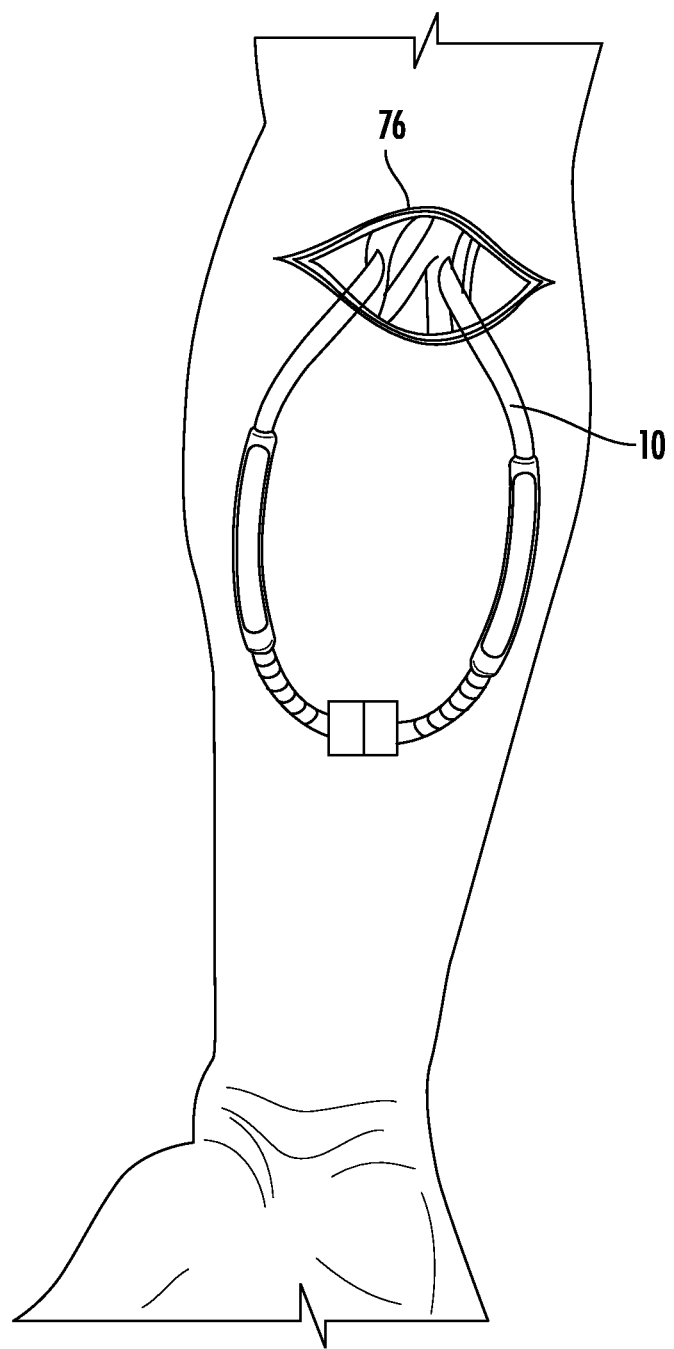

An embodiment of a locking mechanism for use with a looped vascular graft is shown in FIGS. 30 and 31 and generally designated at 800. The locking mechanism 800 is for use with a pair of arcuate tunneling rods 802 schematically shown in FIG. 30. The rods 802 are arranged to be slid along curved paths that mirror one another. The length of the rods 802 depends on the procedure, and particularly on the length of the vascular graft to be inserted. The distal end of each rod 802 is inserted into the exposed tissue at an incision 804. The rods 802 are advanced to a point spaced from the incision 804 with the proximal ends 803 of the rods 802 remaining outside of the body. The distal ends 805 of the rods 802 each carry a portion of the locking mechanism 800. In assembling the pair of rods 802, the locking mechanism 800 components are joined subcutaneously where the distal ends 805 of the rods 802 come together.

Figure 32:
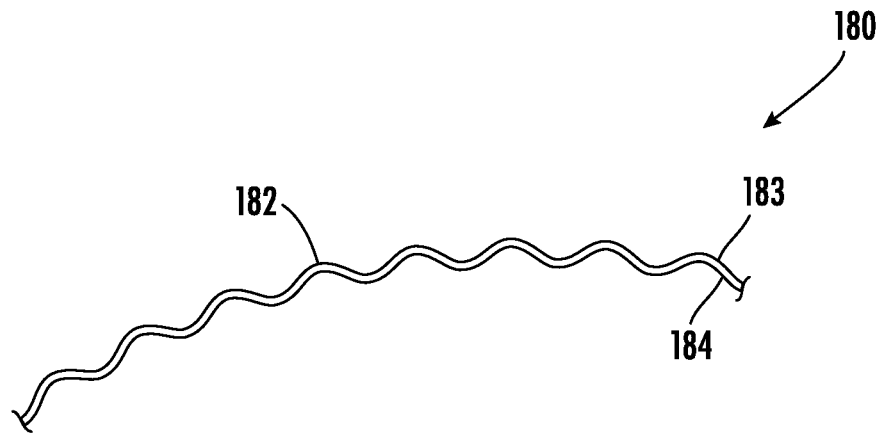
FIG. 32 is a side perspective view of an embodiment of an apparatus for use in forming a subcutaneous anatomical tunnel for implantation of a vascular graft using a helical tunneling device.
Figure 33:
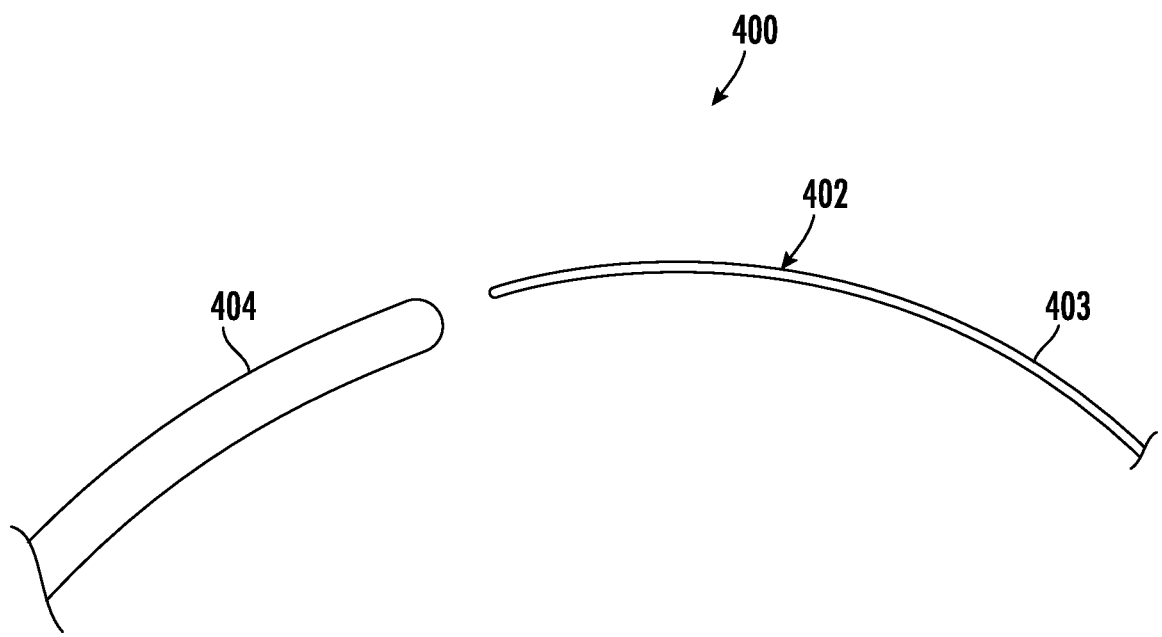
FIG. 33 is a side perspective view of an embodiment of a tunnel forming apparatus showing a guide wire and a sheath.
Figure 34:
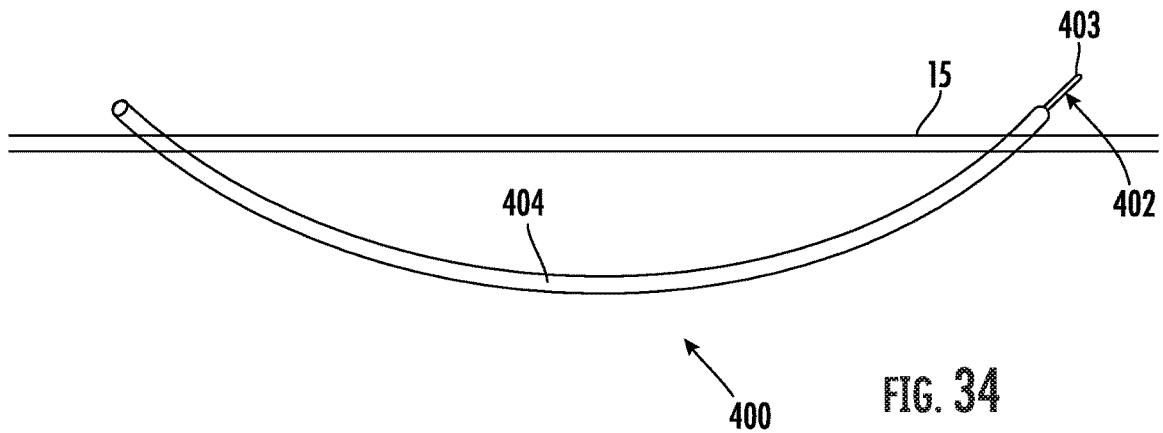
FIG. 34 is a side perspective view of the tunnel forming apparatus as shown in FIG. 30 with the guide wire fully received within the sheath.
Figure 35:
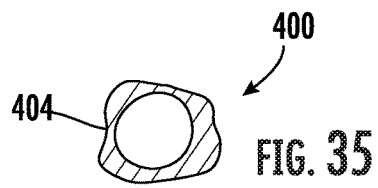
FIG. 35 is a transverse cross-section view of the tunnel forming apparatus as shown in FIG. 31
Figure 36:
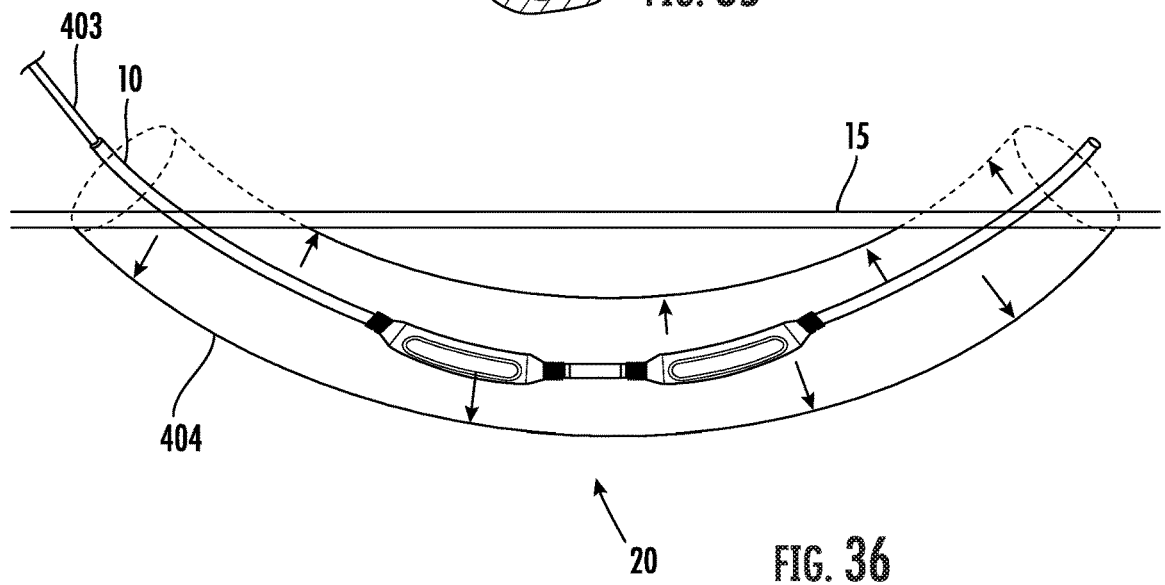
FIG. 36 is a side perspective view of the tunnel forming apparatus as shown in FIG. 31 with the sheath inflated and a vascular graft fully received within the sheath.
Figure 37:
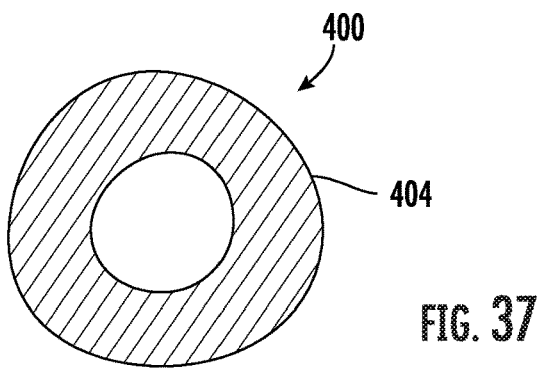
FIG. 37 is a transverse cross-section view of the tunnel forming apparatus as shown in FIG. 33.

A further embodiment of a tunneling apparatus is shown in FIG. 32 and generally designated at 180. The tunneling apparatus 180 comprises a rigid shaft 182 with a tip 184, or nose section, at a distal end 183 of the shaft. In this embodiment, the shaft 182 is fabricated in a helical shape. Thus, the anatomical tunnel formed through the tissue follows a helical path. The vascular graft is then placed within the tissue tunnel in the form of a helical spring.

Yet another embodiment of a tunneling apparatus is shown in FIGS. 33-37 and generally designated at 400. The tunneling apparatus 400 comprises a guide wire 402 and an elongated tubular sheath or conduit 404. The guide wire 402 is substantially rigid for use as a tunneling instrument in creating a subcutaneous tissue path in the patient. The diameter of the guide wire 402 is smaller in comparison to a conventional tunneling instrument to reduce the trauma to the surrounding tissue as the guidewire is pushed through the tissue. The sheath 404 is mounted over the guide wire 402 and encloses the guide wire during a tunneling procedure into the tissue of a patient.

The sheath 404 is formed from a double layer of thin flexible, compressible material closed at both ends and is radially expandable. Accordingly, the sheath 404 has a contracted deployment state, in which the sheath is compressed against the guide wire 402 for use as an insertion tool assembly, and a radially expanded inflated state, which the sheath 404 assumes upon being inflated with a fluid, including a liquid or a gas. The guide wire 402 functions as a means for supporting the sheath 404 in its contracted state during the tunneling step when the tissue is traversed. After the creating the tunnel in tissue, the sheath 404 is inflated, expanding radially outwardly pushing against the tissue walls and providing a clear central hole. In the inflated condition, the sheath 404 is configured for providing an opening of a diameter through which a distal end 403 of the guide wire 402 may be withdrawn for receiving a vascular graft 10 with the application of a reasonable level of axial force. The application of radial force as opposed to longitudinal force in forming the area of the subcutaneous tunnel minimizes trauma to the surrounding tissue and therefore reduces the rate of swelling, pain, and bleeding post-procedure. This facilitates immediate or early cannulation of an implanted vascular graft. Additionally, minimizing the force on the graft 10 during implantation will help to prevent damage to the graft, which may reduce graft stretching and subsequent graft weeping and seroma formation, and help prevent graft kinking.

The sheath 404 may be fabricated from polyethylene, polyvinyl chloride, or other suitable materials well known to those skilled in the art. These materials may further include, but are not limited to, Mylar ribbon, Teflon ribbon, and polypropylene. The smooth outer surface of the material of the sheath 404 may allow the tunneling device 400 to have a low coefficient of friction. The result is easier insertion of the guide wire 402 through the tissue with less trauma, less friction, less blunt dissection and less drag during placement. Due to the smoothness and collapsible low profile of the sheath 404, the sheath does not substantially increase the outside diameter of the tunneling apparatus 400 for deployment. The tunneling apparatus 400 may thus be faster and easier to use, in addition to being less traumatic to tissue. The sheath 404 may also be coated with a lubricous material to further decrease its coefficient of friction and facilitate insertion of the tunneling device 400. The coating aids movement of the sheath 404 and guide wire 402 through the tissue while minimizing tissue drag and trauma during insertion or during sheath 404 removal after implantation. It is understood that a wide variety of coatings are available, including therapeutic agents for delivery of therapeutic materials.

In use, two spaced incisions are first made through the patient's skin into underlying tissue. The distal end 403 of the guide wire 402 with the sheath in the deployment state is inserted into a first incision and then forced horizontally through the subcutaneous tissue along a path until the distal end 403 exits the second incision. The distal end 403 of the guide wire 402 is then attached to a proximal end of the vascular graft 10 by the surgeon, such as, for example, using simple mechanical means, a compression fit collar, staples or sutures or other fastening techniques acceptable for implantation within the tissue of the body. After attachment of the graft 10 to the guide wire 402, the sheath 404 is inflated with fluid forcing the sheath against the dissected tissue defining the tunnel. The expansion of the sheath 404 forms an internal passage through the sheath that is sufficiently large to allow the subsequent withdrawal of the guide wire 402. The guide wire 402 is retracted proximally, which simultaneously draws the attached graft 10 into and through the lumen of the inflated hollow sheath 20 until the proximal end of the graft 10 exits the first incision. The inflated sheath 204 allows the surgeon to easily pull the vascular graft 10 through the internal lumen defined by the sheath 204, which is substantially oversized in comparison to the outside diameter of the vascular graft 10. Once the graft 10 has been drawn to the site of the first incision, the proximal end of the graft 10 is disconnected from the distal end 203 of the guide wire 202.

Next, the sheath 204 is deflated and extracted from the subcutaneous tissue path without extracting the graft 10. Specifically, the surgeon holds the graft 10 in place by grasping a distal end of the graft extending from the second incision and pulls the sheath 204 through the first incision. The graft 10 remains within the anatomic subcutaneous tunnel. With the sheath 204 removed, the tissue collapses against the outer surface of the graft 10. The surgeon now forms anastomoses at each end of the graft 10 by suturing the ends of the graft to a blood vessel at the desired locations.

The embodiments of the tunneling apparatus as described herein are shown in use for procedures with a vascular graft suitable for implantation in the body and used to reestablish or redirect the flow of blood beyond the blockage area. It is understood that the several tunneling apparatus described and shown herein may be used in other surgical implantation procedures requiring placement of the vascular graft within the subcutaneous tissue. One of ordinary skill in the art will recognize that the embodiments of the tunneling apparatus as described are not directed to a specific vascular graft design, but are generically applicable to many different types of vascular grafts, which may be a synthetic graft constructed from different materials or a natural tissue graft.

The tunneling apparatus and methods as described have many advantages, including a reduction of friction and resistance, and related tissue damage, during the passage of the tunneling device when forming a an anatomical tunnel. The tunneling apparatus and methods may help to reduce swelling and damage to the surrounding tissue, which would facilitate immediate or early cannulation of a subsequently implanted vascular graft.

We claim:

1. An apparatus for subcutaneous implantation in a patient for use with a tunneling instrument including a shaft having a proximal end and a distal end, the implantation apparatus comprising:
   a vascular arteriovenous graft having a proximal end and a distal end and a length between the proximal end and the distal end; and
   a connector adapted to couple the distal end of the tunneling instrument and the proximal end of the graft, the connector comprising
      a tip comprising a first end, a second end and an intermediate portion between the first end and the second end, the intermediate portion having a reduced diameter forming a circumferential groove around a periphery of the tip, the first end of the tip configured to be received within the proximal end of graft,
      a clip sized and shaped to provide a snap-fit connection within the groove of the tip, a portion of the proximal end of the graft receiving the tip being positioned between the clip and the tip within the groove for securing the graft to the tip, and
      a coupler for connection of the tip to the tunneling instrument such that the tip and the graft are rotatable about their longitudinal axes relative to the coupler and the tunneling instrument.

2. An apparatus for subcutaneous implantation in a patient using a tunneling instrument including a shaft having a proximal end and a distal end, the implantation apparatus comprising:
   a vascular arteriovenous graft having a proximal end and a distal end and a length between the proximal end and the distal end;
   a connector adapted to couple the distal end of the tunneling instrument and the proximal end of the graft, the connector comprising
      a tip is adapted to be removably attached to the distal end of the tunneling instrument, and
      a coupler for a rotatable connection of the tip to the tunneling instrument such that the tip is rotatable about its longitudinal axis relative to the coupler,
   wherein the connector is configured for connecting the graft to the tunneling instrument upon removal of the tip.

3. The implantation apparatus as recited in claim 1, wherein the connector comprises a frustoconical cone having an axial opening for receiving the graft, a length of the cone including a screw thread formed on an external surface for connection of the cone to the tunneling instrument, wherein a portion of the graft is positioned between the threads of the cone and the tunneling instrument to fix the graft to the tip.

4. The implantation apparatus as recited in claim 1, wherein the coupler comprises a hollow sleeve for rotatable connection to the tunneling instrument, and further comprising
   a plug received within the proximal end of the graft, the sleeve configured for receiving the plug such that a portion of the graft is positioned between the plug and the sleeve to fix the graft in the sleeve.

* * * * *

UNITED STATES PATENT AND TRADEMARK OFFICE
CERTIFICATE OF CORRECTION

| | |
|---|---|
| PATENT NO. | : 11,045,339 B2 |
| APPLICATION NO. | : 16/723211 |
| DATED | : June 29, 2021 |
| INVENTOR(S) | : Shawn M. Gage et al. |

It is certified that error appears in the above-identified patent and that said Letters Patent is hereby corrected as shown below:

In the Specification

Please insert the following in Column 1, Line 12:
--Government Rights
This invention was made with government support under contract number NIH R41DK108488 awarded by the National Institute of Health. The government has certain rights in the invention.--

Signed and Sealed this
Nineteenth Day of July, 2022

Katherine Kelly Vidal
*Director of the United States Patent and Trademark Office*